US011673922B2

(12) United States Patent
Bowen et al.

(10) Patent No.: US 11,673,922 B2
(45) Date of Patent: Jun. 13, 2023

(54) INSECT INHIBITORY PROTEINS

(71) Applicant: Monsanto Technology LLC, St. Louis, MO (US)

(72) Inventors: David J. Bowen, Wildwood, MO (US); Todd A. Ciche, San Diego, CA (US); Arlene R. Howe, Clarkson Valley, MO (US); Stephanie C. Waldheuser, St. Louis, MO (US); Kimberly M. Wegener, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 17/561,332

(22) Filed: Dec. 23, 2021

(65) Prior Publication Data

US 2022/0220160 A1    Jul. 14, 2022

Related U.S. Application Data

(60) Provisional application No. 63/132,877, filed on Dec. 31, 2020.

(51) Int. Cl.
| | | |
|---|---|---|
| *C07K 14/32* | (2006.01) | |
| *C12N 15/82* | (2006.01) | |
| *A01P 7/04* | (2006.01) | |
| *A01N 63/50* | (2020.01) | |
| *C07K 14/325* | (2006.01) | |

(52) U.S. Cl.
CPC ............ *C07K 14/325* (2013.01); *A01N 63/50* (2020.01); *A01P 7/04* (2021.08); *C12N 15/8286* (2013.01)

(58) Field of Classification Search
CPC .. A01N 63/50; C07K 14/325; C12N 15/8286; A01P 7/04
See application file for complete search history.

(56) References Cited

U.S. PATENT DOCUMENTS

| | | |
|---|---|---|
| 5,188,642 A | 2/1993 | Shah et al. |
| 5,312,910 A | 5/1994 | Kishore et al. |
| 5,500,365 A | 3/1996 | Fischhoff et al. |
| 5,627,061 A | 5/1997 | Barry et al. |
| 5,633,435 A | 5/1997 | Barry et al. |
| 5,728,925 A | 3/1998 | Herrera-Estrella et al. |
| 5,750,871 A | 5/1998 | Moloney et al. |
| 5,880,275 A | 3/1999 | Fischhoff et al. |
| 6,033,874 A | 3/2000 | Baum et al. |
| 6,365,807 B1 | 4/2002 | Christou et al. |
| 6,501,009 B1 | 12/2002 | Romano |
| 6,551,962 B1 | 4/2003 | Pershing et al. |
| 6,713,063 B1 | 3/2004 | Malvar et al. |
| 6,962,705 B2 | 11/2005 | Malvar et al. |
| 7,026,528 B2 | 4/2006 | Cheng et al. |
| 7,064,249 B2 | 6/2006 | Corbin et al. |
| 7,070,982 B2 | 7/2006 | Malvar et al. |
| 7,193,133 B2 | 3/2007 | Lassner et al. |
| 7,510,878 B2 | 3/2009 | Abad et al. |
| 7,772,465 B2 | 8/2010 | Abad et al. |
| 7,812,129 B1 | 10/2010 | Abad et al. |
| 8,344,207 B2 | 1/2013 | Bogdanova et al. |
| 8,609,936 B2 | 12/2013 | Baum et al. |
| 10,059,959 B2 | 8/2018 | Baum et al. |
| 10,155,960 B2 | 12/2018 | Bowen et al. |
| 10,227,608 B2 | 3/2019 | Barry et al. |
| 10,233,217 B2 | 3/2019 | Baum et al. |
| 10,494,408 B2 | 12/2019 | Baum et al. |
| 10,611,806 B2 | 4/2020 | Baum et al. |
| 10,669,317 B2 | 6/2020 | Baum et al. |
| 10,703,782 B2 | 7/2020 | Baum et al. |
| 2001/0042257 A1 | 11/2001 | Connor-Ward et al. |
| 2003/0110531 A1 | 6/2003 | Dan et al. |
| 2006/0021087 A1 | 1/2006 | Baum et al. |
| 2006/0112447 A1 | 5/2006 | Bogdanova et al. |
| 2008/0172762 A1 | 7/2008 | Cerf et al. |
| 2008/0256667 A1 | 10/2008 | Dersch et al. |

(Continued)

FOREIGN PATENT DOCUMENTS

| | | |
|---|---|---|
| EP | 0218571 | 2/1993 |
| EP | 0189707 | 8/1993 |

(Continued)

OTHER PUBLICATIONS

Guo et al., 2004, Protein tolerance to random amino acid change. Proceedings of the National Academy of Sciences, 101(25), 9205-9210. (Year: 2004).*

Pillai-Kastoori et al., 2020, Antibody validation for Western blot: By the user, for the user. Journal of Biological Chemistry, 295(4), 926-939. (Year: 2020).*

Saper et al., 2005, An open letter to our readers on the use of antibodies. J. Comp. Neurol. 493, 477-478 (Year: 2005).*

Argôlo-Filho and Loguercio, 2013, Bacillus thuringiensis is an environmental pathogen and host-specificity has developed as an adaptation to human-generated ecological niches. Insects, 5(1), 62-91. (Year: 2013).*

(Continued)

*Primary Examiner* — Cathy Kingdon Worley
*Assistant Examiner* — Santosh Sharma
(74) *Attorney, Agent, or Firm* — Dentons US LLP; Timothy K. Ball

(57) ABSTRACT

Pesticidal proteins exhibiting toxic activity against Lepidopteran pest species are disclosed, and include, but are not limited to, TIC13085 and TIC13087. DNA constructs are provided which contain a recombinant nucleic acid sequence encoding one or more of the disclosed pesticidal proteins. Transgenic plants, plant cells, seed, and plant parts resistant to Lepidopteran infestation are provided which contain recombinant nucleic acid sequences encoding the pesticidal proteins of the present invention. Methods for detecting the presence of the recombinant nucleic acid sequences or the proteins of the present invention in a biological sample, and methods of controlling Lepidopteran species pests using any of the TIC13085 and TIC13087 pesticidal proteins are also provided.

29 Claims, No Drawings

Specification includes a Sequence Listing.

(56) References Cited

U.S. PATENT DOCUMENTS

| | | |
|---|---|---|
| 2008/0280361 A1 | 11/2008 | Calabotta et al. |
| 2008/0282432 A1 | 11/2008 | Duncan et al. |
| 2009/0138985 A1 | 5/2009 | Martinell et al. |
| 2009/0142837 A1 | 6/2009 | Adams et al. |
| 2009/0313721 A1 | 12/2009 | Abad et al. |
| 2010/0004176 A1 | 1/2010 | Sampson et al. |
| 2010/0017914 A1 | 1/2010 | Hart et al. |
| 2010/0077507 A1 | 3/2010 | Abad et al. |
| 2010/0077508 A1 | 3/2010 | Abad et al. |
| 2010/0137216 A1 | 6/2010 | Carozzi et al. |
| 2010/0160231 A1 | 6/2010 | Sampson et al. |
| 2010/0192256 A1 | 7/2010 | Abad et al. |
| 2010/0197592 A1 | 8/2010 | Heinrichs |
| 2010/0269221 A1 | 10/2010 | Abad et al. |
| 2010/0317569 A1 | 12/2010 | Lira et al. |
| 2010/0319092 A1 | 12/2010 | Lira et al. |
| 2010/0319093 A1 | 12/2010 | Lira et al. |
| 2011/0030096 A1 | 2/2011 | Sampson et al. |
| 2011/0055968 A1 | 3/2011 | Cerf et al. |
| 2011/0112013 A1 | 5/2011 | Abad et al. |
| 2011/0154536 A1 | 6/2011 | Abad et al. |
| 2012/0047606 A1 | 2/2012 | Abad et al. |
| 2012/0117690 A1 | 5/2012 | Cerf et al. |
| 2012/0167259 A1 | 6/2012 | Liu et al. |
| 2012/0192310 A1 | 7/2012 | Abad et al. |
| 2012/0210462 A1 | 8/2012 | Bermudez et al. |
| 2012/0233726 A1 | 9/2012 | Abad et al. |
| 2012/0266335 A1* | 10/2012 | Larrinua ............... A23D 9/00 530/370 |
| 2013/0055469 A1 | 2/2013 | Sampson et al. |
| 2013/0097735 A1 | 4/2013 | Bowen et al. |
| 2013/0104259 A1 | 4/2013 | Sampson et al. |
| 2013/0117884 A1 | 5/2013 | Hargiss et al. |
| 2013/0167264 A1 | 6/2013 | Sampson et al. |
| 2013/0219570 A1 | 8/2013 | Lira et al. |
| 2013/0269060 A1 | 10/2013 | Baum et al. |
| 2013/0303440 A1 | 11/2013 | Sampson et al. |
| 2013/0310543 A1 | 11/2013 | Sampson et al. |
| 2014/0007292 A1 | 1/2014 | Cerf et al. |
| 2014/0033361 A1 | 1/2014 | Altier et al. |
| 2014/0033363 A1 | 1/2014 | Sampson |
| 2014/0196175 A1 | 7/2014 | Sampson et al. |
| 2014/0223598 A1 | 8/2014 | Sampson et al. |
| 2014/0223599 A1 | 8/2014 | Sampson et al. |
| 2014/0245491 A1 | 8/2014 | Sampson et al. |
| 2014/0298538 A1 | 10/2014 | Heinrichs et al. |
| 2014/0366227 A1 | 12/2014 | Gatehouse et al. |
| 2014/0373195 A1 | 12/2014 | Sampson et al. |
| 2016/0366891 A1 | 12/2016 | Diehn et al. |
| 2018/0100000 A1* | 4/2018 | Bowen ............... G01N 33/5308 |
| 2019/0055577 A1 | 2/2019 | Bowen et al. |
| 2020/0229445 A1 | 7/2020 | Bowen et al. |
| 2022/0192200 A1* | 6/2022 | Bowen ............... A01P 7/04 |

FOREIGN PATENT DOCUMENTS

| | | |
|---|---|---|
| EP | 0508909 | 8/1998 |
| EP | 0924299 | 5/2004 |
| WO | 2013134523 | 9/2013 |
| WO | 2014008054 A2 | 1/2014 |
| WO | 2015195594 A2 | 12/2015 |
| WO | 2016061391 A2 | 4/2016 |
| WO | 2016061392 A1 | 4/2016 |
| WO | 2019178038 A1 | 9/2019 |

OTHER PUBLICATIONS

Sambrook et al. (2006). The condensed protocols: from molecular cloning: a laboratory manual (Third Edition). Cold Spring Harbor, NY: Cold spring harbor laboratory press. (Year: 2006).*

Gryson et al., 2002, Detection of DNA during the refining of soybean oil. Journal of the American Oil Chemists' Society, 79(2), 171-174. (Year: 2002).*

Alphey, et al. Combining Pest Control and Resistance Management: Synergy of Engineered Insects With Bt Crops, Journal of Economic Entomology, vol. 102, Issue 2, pp. 717-732, 2009.

Arencibia, et al. An efficient protocol for sugarcane (*Saccharum* spp. L.) transformation mediated by Agrobacterium tumefaciens. Transgenic Res 7, 213-222 (1998).

Della-Cioppa, et al. Translocation of the precursor of 5-enolpyruvylshikimate-3-phosphate synthase into chloroplasts of higher plants in vitro. PNAS, vol. 83, No. 18 (1986).

Estruch, et al. Vip3A, a novel Bacillus thuringiensis vegetative insecticidal protein with a wide spectrum of activities against lepidopteran insects. PNAS, vol. 93, No. 11 (1996).

ISAAA, 2016. Global Status of Commercialized Biotech/ GM Crops: 2016. ISAAA Brief No. 52 ISAAA: Ithaca, NY.

Jin, et al. Engineered Female-Specific Lethality for Control of Pest Lepidoptera. ACS Synth. Biol. 2013, 2, 3, 160-166 (2013).

Klee, et al. Cloning of an *Arabidopsis thaliana* gene encoding 5-enolpyruvylshikimate-3-phosphate synthase: sequence analysis and manipulation to obtain glyphosate-tolerant plants. Mol Gen Genet 210, 437-442 (1987).

Thompson, et al. CLUSTAL W: improving the sensitivity of progressive multiple sequence alignment through sequence weighting, position-specific gap penalties and weight matrix choice. Nucleic Acids Research, vol. 22, Issue 22, pp. 4673-4680, (1994).

Zhou, et al. Combining the high-dose/refuge strategy and self-limiting transgenic insects in resistance management—A test in experimental mesocosms. Evolutionary Applications, vol. 11, Issue 5, pp. 727-738, (2018).

GenBank Accession No. WP_119791737, dated Jul. 24, 2021.

International Search Report and Written Opinion regarding International App. No. PCT/US21/65096, dated May 23, 2022.

UniProtKB Accession No. A0A3A3GLR0_PANTH, dated Dec. 11, 2019.

* cited by examiner

SEQUENCE LISTING

```
<160> NUMBER OF SEQ ID NOS: 6

<210> SEQ ID NO 1
<211> LENGTH: 2412
<212> TYPE: DNA
<213> ORGANISM: Bacillus thuringiensis
<220> FEATURE:
<221> NAME/KEY: misc_feature
<222> LOCATION: (1)..(2412)
<223> OTHER INFORMATION: Nucleic acid sequence encoding a TIC13085
      pesticidal protein obtained from Bacillus thuringiensis.

<400> SEQUENCE: 1
atgaagcaga ataataattt aagtgtaaga gccttaccag gttttattga tgttttcaat     60
ggaatttatg gttttgccac tggtattcaa gatattatta acatgatttt tagaacagat    120
acaggtgatc taacactgga agaagtttta aaaaatcaag atttacttaa tcatatttct    180
ggtaaacttg atgggattaa tggagaccta agtgagatta ttgcgcaggg aaatttgaat    240
acagaattag ctaaggaatt gctaaaaatc gctaatgagc agaacaatgt attaactgat    300
gttaataaca aactcaatgc gataaatgcg atgctcaaca catatcttcc taaaattaca    360
aatatgttaa gcgatattat gaaacaaaat tatgtcctga gtcttcaaat agaatatctc    420
agtaaacaac tacaggagat ttcagataaa cttgatgtta ttaatttaaa tgtactcatc    480
aactctacac tcacagaaat cactcctgct tatcaacgta ttaaatatgt aaatgaaaaa    540
tttgatgaat taactcttgc tacagaaaaa actctaagag caaaacaagg tagttttaac    600
gaagatgttt ttgataatga tactcttgat aatttaactg agctaactga actagcgaaa    660
agtgtaacaa aaaatgacgt agatagtttc gagttttatc tccatacatt ccatgatgtt    720
ttgattggca ataatttatt tggacgttcg gcttaaaaaa cagcttctga attaattact    780
aaagacgaga taaagacgag tggaagtgag ataggaaaag tttatagttt cttaattgta    840
ttaacttgtt tacaagcaaa agcctttctc actttaacgg catgccgaaa attattgggc    900
```

```
ctaacagata ttgattatac taatattcta gatcagcatc taaatgatga aaaaaatgag    960
tttcgtgtaa acatacttcc tacactgtcc aataaatttt ctaaccctaa ttatgcaaaa   1020
actataggaa gtgataatta tgcaaaagtt actttagaag ctgaaccagg atatgcttta   1080
gttggatttg aaattattaa tgatccaatc ccggtattaa aagggtacca agctaagcta   1140
aaacaaaatt atcaagttga taatcagtcg ttatcaggga ttgtttattt taatatcgat   1200
aaactactgt gtccgaataa atctgaacaa aaatattata ctaaaagtct gacatttcct   1260
gatggctatg ttattactaa aattaccttt gaaaaaaagc tgaacaacct aagatatgag   1320
gcaacagcaa atttttatga tccatctaca ggaattatag atttaaataa gaagcaagtg   1380
gaatctactt ttcttcaaga gaaatatatc ggtttaaacg ctagtgatga tggtgtttat   1440
atgccgttag gcgttatcag cgaaacgttt ttgtctccaa tcaatagttt tgaattagat   1500
gttaatgaga aatcgaaaat attaacttta acatgtaaat cttatctacg agaatatcta   1560
ttagaaactg atttaataaa taaagagaca agcctgattg ttccacctaa ttttagcaat   1620
atagtagaaa atggggacat aagagcagac agtttagaac catggaaagc aaataacaaa   1680
aatgcatatg tcgatattac aggtggtgtg aatggatcta aagccctcta tacttatggt   1740
gatggggaat tctcacaatt tattggagat aaactaaaac ctaagacaga ttatattatt   1800
caatatactg taaaaggaaa acctgctatt tatttaaaac acaaaaatac tactgactat   1860
attatgtatg aagatacaaa cggtaattat gaagattttc aaactaagac tgtaaaatat   1920
acttcaggaa ctgatccctc accagcacat ttggttttta aaaatcagag tggctatgag   1980
gcttgggggg acaaatttat tattttagaa gctaagctat ttgaaactcc agaaactcca   2040
gaaagtccag aattgataaa atttgataat tggattaaga gtgggaattc taatgaatct   2100
tggatttctg gagatacatt cgttctctat aatccgaatg gatcttttag acaaaatctt   2160
caattagaca gtttttcaac ttataacttg agcttttctt ttagtggtat aaggggtaag   2220
gttacaataa aaaattcccg agaagtatta tttgaaaaag agtatgtgta cgaaggtctt   2280
ggatttcatg ataagactga aagttttact accgcatcaa ataaagatgg attctttata   2340
gaacttacga ctactacgta ttctactcag aattctttcc gtaatttttc tattaaagaa   2400
aaacttgagt ag                                                        2412
```

```

<210> SEQ ID NO 2
<211> LENGTH: 803
<212> TYPE: PRT
<213> ORGANISM: Bacillus thuringiensis
<220> FEATURE:
<221> NAME/KEY: MISC_FEATURE
<222> LOCATION: (1)..(803)
<223> OTHER INFORMATION: Amino acid sequence of the TIC13085 pesticidal
      protein.

<400> SEQUENCE: 2

Met Lys Gln Asn Asn Asn Leu Ser Val Arg Ala Leu Pro Gly Phe Ile
1               5                   10                  15

Asp Val Phe Asn Gly Ile Tyr Gly Phe Ala Thr Gly Ile Gln Asp Ile
            20                  25                  30

Ile Asn Met Ile Phe Arg Thr Asp Thr Gly Asp Leu Thr Leu Glu Glu
        35                  40                  45

Val Leu Lys Asn Gln Asp Leu Leu Asn His Ile Ser Gly Lys Leu Asp
    50                  55                  60

Gly Ile Asn Gly Asp Leu Ser Glu Ile Ile Ala Gln Gly Asn Leu Asn
```

```
            65                  70                  75                  80
Thr Glu Leu Ala Lys Glu Leu Lys Ile Ala Asn Glu Gln Asn Asn
                    85                  90                  95
Val Leu Thr Asp Val Asn Asn Lys Leu Asn Ala Ile Asn Ala Met Leu
                    100                 105                 110
Asn Thr Tyr Leu Pro Lys Ile Thr Asn Met Leu Ser Asp Ile Met Lys
                    115                 120                 125
Gln Asn Tyr Val Leu Ser Leu Gln Ile Glu Tyr Leu Ser Lys Gln Leu
            130                 135                 140
Gln Glu Ile Ser Asp Lys Leu Asp Val Ile Asn Leu Asn Val Leu Ile
145                 150                 155                 160
Asn Ser Thr Leu Thr Glu Ile Thr Pro Ala Tyr Gln Arg Ile Lys Tyr
                    165                 170                 175
Val Asn Glu Lys Phe Asp Glu Leu Thr Leu Ala Thr Glu Lys Thr Leu
                    180                 185                 190
Arg Ala Lys Gln Gly Ser Phe Asn Glu Asp Val Phe Asp Asn Asp Thr
                    195                 200                 205
Leu Asp Asn Leu Thr Glu Leu Thr Glu Leu Ala Lys Ser Val Thr Lys
            210                 215                 220
Asn Asp Val Asp Ser Phe Glu Phe Tyr Leu His Thr Phe His Asp Val
225                 230                 235                 240
Leu Ile Gly Asn Asn Leu Phe Gly Arg Ser Ala Leu Lys Thr Ala Ser
                    245                 250                 255
Glu Leu Ile Thr Lys Asp Glu Ile Lys Thr Ser Gly Ser Glu Ile Gly
                    260                 265                 270
Lys Val Tyr Ser Phe Leu Ile Val Leu Thr Cys Leu Gln Ala Lys Ala
                    275                 280                 285
Phe Leu Thr Leu Thr Ala Cys Arg Lys Leu Leu Gly Leu Thr Asp Ile
            290                 295                 300
Asp Tyr Thr Asn Ile Leu Asp Gln His Leu Asn Asp Glu Lys Asn Glu
305                 310                 315                 320
Phe Arg Val Asn Ile Leu Pro Thr Leu Ser Asn Lys Phe Ser Asn Pro
                    325                 330                 335
Asn Tyr Ala Lys Thr Ile Gly Ser Asp Asn Tyr Ala Lys Val Thr Leu
                    340                 345                 350
Glu Ala Glu Pro Gly Tyr Ala Leu Val Gly Phe Glu Ile Ile Asn Asp
            355                 360                 365
Pro Ile Pro Val Leu Lys Gly Tyr Gln Ala Lys Leu Lys Gln Asn Tyr
        370                 375                 380
Gln Val Asp Asn Gln Ser Leu Ser Gly Ile Val Tyr Phe Asn Ile Asp
385                 390                 395                 400
Lys Leu Leu Cys Pro Asn Lys Ser Glu Gln Lys Tyr Tyr Thr Lys Ser
                    405                 410                 415
Leu Thr Phe Pro Asp Gly Tyr Val Ile Thr Lys Ile Thr Phe Glu Lys
                    420                 425                 430
Lys Leu Asn Asn Leu Arg Tyr Glu Ala Thr Ala Asn Phe Tyr Asp Pro
            435                 440                 445
Ser Thr Gly Ile Ile Asp Leu Asn Lys Lys Gln Val Glu Ser Thr Phe
        450                 455                 460
Leu Gln Glu Lys Tyr Ile Gly Leu Asn Ala Ser Asp Asp Gly Val Tyr
465                 470                 475                 480
Met Pro Leu Gly Val Ile Ser Glu Thr Phe Leu Ser Pro Ile Asn Ser
                    485                 490                 495
```

Phe Glu Leu Asp Val Asn Glu Lys Ser Lys Ile Leu Thr Leu Thr Cys
                500                 505                 510

Lys Ser Tyr Leu Arg Glu Tyr Leu Glu Thr Asp Leu Ile Asn Lys
        515                 520                 525

Glu Thr Ser Leu Ile Val Pro Pro Asn Phe Ser Asn Ile Val Glu Asn
    530                 535                 540

Gly Asp Ile Arg Ala Asp Ser Leu Glu Pro Trp Lys Ala Asn Asn Lys
545                 550                 555                 560

Asn Ala Tyr Val Asp Ile Thr Gly Val Asn Gly Ser Lys Ala Leu
            565                 570                 575

Tyr Thr Tyr Gly Asp Gly Glu Phe Ser Gln Phe Ile Gly Asp Lys Leu
            580                 585                 590

Lys Pro Lys Thr Asp Tyr Ile Ile Gln Tyr Thr Val Lys Gly Lys Pro
        595                 600                 605

Ala Ile Tyr Leu Lys His Lys Asn Thr Thr Asp Tyr Ile Met Tyr Glu
    610                 615                 620

Asp Thr Asn Gly Asn Tyr Glu Asp Phe Gln Thr Lys Thr Val Lys Tyr
625                 630                 635                 640

Thr Ser Gly Thr Asp Pro Ser Pro Ala His Leu Val Phe Lys Asn Gln
            645                 650                 655

Ser Gly Tyr Glu Ala Trp Gly Asp Lys Phe Ile Ile Leu Glu Ala Lys
            660                 665                 670

Leu Phe Glu Thr Pro Glu Thr Pro Glu Ser Pro Glu Leu Ile Lys Phe
        675                 680                 685

Asp Asn Trp Ile Lys Ser Gly Asn Ser Asn Glu Ser Trp Ile Ser Gly
    690                 695                 700

Asp Thr Phe Val Leu Tyr Asn Pro Asn Gly Ser Phe Arg Gln Asn Leu
705                 710                 715                 720

Gln Leu Asp Ser Phe Ser Thr Tyr Asn Leu Ser Phe Ser Phe Ser Gly
            725                 730                 735

Ile Arg Gly Lys Val Thr Ile Lys Asn Ser Arg Glu Val Leu Phe Glu
            740                 745                 750

Lys Glu Tyr Val Tyr Glu Gly Leu Gly Phe His Asp Lys Thr Glu Ser
        755                 760                 765

Phe Thr Thr Ala Ser Asn Lys Asp Gly Phe Phe Ile Glu Leu Thr Thr
    770                 775                 780

Thr Thr Tyr Ser Thr Gln Asn Ser Phe Arg Asn Phe Ser Ile Lys Glu
785                 790                 795                 800

Lys Leu Glu

<210> SEQ ID NO 3
<211> LENGTH: 2409
<212> TYPE: DNA
<213> ORGANISM: Bacillus thuringiensis
<220> FEATURE:
<221> NAME/KEY: misc_feature
<222> LOCATION: (1)..(2409)
<223> OTHER INFORMATION: Nucleic acid sequence encoding a TIC13087
      pesticidal protein obtained from Bacillus thuringiensis.

<400> SEQUENCE: 3
atgaagcaga ataataattt aagtgtaaga gccttaccaa tttggattga tgttttaat       60 ggaatttatg gttttccac tggtattcaa gatattttta acatgatttt tggaacagat      120
acaggtgatt taacactaga agaagttttg aaaaatcaag atttacttaa tgagatttct      180

```
ggtaaacttg atgggattaa tggagaccta agtgaaatta ttgcgcaggg aaatttgaat      240
acagaatcaa ctaaggaatt gctaaaaatc gctaatgagc agaacaattt attaactgat      300
gtaaataaca aactcaatgc gataaatgcg atgcttaaca catatcttcc taaaattaca      360
aatatgttaa gcgatattat gaaacaaaat tatgtcctaa gtcttcaatt agaatatctc      420
agtaaacaac tacaggagat ttcagataaa cttgatgtta ttaatttaaa tgtactcatc      480
aactctacac tcacagaaat cactcctgct tatcaacgta ttaaatatgt aaacgaaaaa      540
tttgatgact taactcttgc tacagaaaaa actctaagag caaacaagg tagctttaac       600 gaagatattt ttgataatga tactcttgaa aatttaactg agctaactga actagcgaaa      660
agtgtaacaa aaaatgacgt ggatagtttc gagttttatc tccatacatt ccatgatgta      720
ttgattggca ataatttatt tggtcgttcg gcttttaaaaa cagctgcaga attgattact      780
aaagacgaga taaagacgag tggaagtgag ataggaaaag tttatagttt cttaattgta      840
ctaacttgtc tacaagcaaa agcctttctc actttaacgg catgccgaaa attattgggc      900
ttatcagata ttgattatac taatattcta aatcagcatc taaatgagga aaagaatgta      960
tttcgtgata acatacttcc tacactgtcc aataaatttt ctaaccctaa ttatgtaaaa     1020
actataggta gtgataatta tgcaaaagtt attttagaag ctgaaccagg atatgcttta     1080
gttggatttg aaattatcaa tgatccaatc ccggtattaa aagcgtatca agctaagcta     1140
aaacaaaatt atcaagttga taatcagtcg ttatcgagaa ttgtttattt agatatcgat     1200
aaactattct gtccaaaaaa ttctgaacaa agtattata ctaaaagtct gacatttcct      1260
gatggctatg ttattactaa gattaccttt gaaaaaaagc tgaacaacct aagatatgag     1320
gcaacagcaa attttatga cccatctaca ggagctattg atttaaatga aagcaagtg       1380 gaatctactt ttcttaaagc agattatatt tcaataaatg ttagtgatga tgatgatgat     1440
ggtgtttaca tgccgttagg cgttatcagc gaaacatttt tgtctccaat taatagttt      1500 gaattagaag ttgacgagaa atcgaaaatc ttaactttaa catgtaaatc ttatttacga     1560
gaatatttat tagaatctga tttaataaat aaagagacaa gcctcattgc tccgcctaat     1620 gttttttatca gtaatatcgt agaaaattgg aatatagaag cggataatct agaaccatgg    1680
gtagcaaata acaagaatgc atatgtcgat agtacaggcg gcatagaggg atctaaagct    1740
ctatttgctc aaggtgatgg ggaattttca caatttattg gagataaatt aaaaccaaat     1800
acagattata tgattcaata tactgtaaaa ggaaaacctg ccatttattt aaaaaacaaa     1860
aatactggat atactatgta cgaagataca aacggtagtt ctgaagaatt tcaaactata     1920
gctgtaaatt atacttcaga aactgatcct tcacaaacac atttagtttt taaaagtcaa     1980
agtggctatg aggcttgggg ggacaacttt attattctag aaagtaaggc attttgaaact    2040 ccagaaggtc cagaattgat aaaatttgat aattggactc gatctggcgg cactttcata    2100
agcggaaacg aacttgttat aaatgctagg aatggtaact ttagacaaaa tattcaatta     2160
ggcagtttct caactataa tatgagtttt tcaattcggg gagcgtgtag ggttaggata      2220
tcaaatcaag gtacaacaat atttcaacaa gattatcatg atactaccta tataaatatt     2280
actgaaagtt tcactaccaa aaccatttca agtacatccc ttatagaatt ttcttcgccc    2340
aatctttcta ccccttataa taatgcgtat ggtcgagatt tttcaattag ggaaaaaata    2400
gaattttaa                                                             2409
```

<210> SEQ ID NO 4
<211> LENGTH: 802

```
<212> TYPE: PRT
<213> ORGANISM: Bacillus thuringiensis
<220> FEATURE:
<221> NAME/KEY: MISC_FEATURE
<222> LOCATION: (1)..(802)
<223> OTHER INFORMATION: Amino acid sequence of the TIC13087 pesticidal
      protein.

<400> SEQUENCE: 4
```

Met Lys Gln Asn Asn Asn Leu Ser Val Arg Ala Leu Pro Ile Trp Ile
1               5                   10                  15

Asp Val Phe Asn Gly Ile Tyr Gly Phe Ser Thr Gly Ile Gln Asp Ile
            20                  25                  30

Phe Asn Met Ile Phe Gly Thr Asp Thr Gly Asp Leu Thr Leu Glu Glu
        35                  40                  45

Val Leu Lys Asn Gln Asp Leu Leu Asn Glu Ile Ser Gly Lys Leu Asp
    50                  55                  60

Gly Ile Asn Gly Asp Leu Ser Glu Ile Ile Ala Gln Gly Asn Leu Asn
65                  70                  75                  80

Thr Glu Ser Thr Lys Glu Leu Leu Lys Ile Ala Asn Glu Gln Asn Asn
                85                  90                  95

Leu Leu Thr Asp Val Asn Asn Lys Leu Asn Ala Ile Asn Ala Met Leu
            100                 105                 110

Asn Thr Tyr Leu Pro Lys Ile Thr Asn Met Leu Ser Asp Ile Met Lys
        115                 120                 125

Gln Asn Tyr Val Leu Ser Leu Gln Leu Glu Tyr Leu Ser Lys Gln Leu
    130                 135                 140

Gln Glu Ile Ser Asp Lys Leu Asp Val Ile Asn Leu Asn Val Leu Ile
145                 150                 155                 160

Asn Ser Thr Leu Thr Glu Ile Thr Pro Ala Tyr Gln Arg Ile Lys Tyr
                165                 170                 175

Val Asn Glu Lys Phe Asp Asp Leu Thr Leu Ala Thr Glu Lys Thr Leu
            180                 185                 190

Arg Ala Lys Gln Gly Ser Phe Asn Glu Asp Ile Phe Asp Asn Asp Thr
        195                 200                 205

Leu Glu Asn Leu Thr Glu Leu Thr Glu Leu Ala Lys Ser Val Thr Lys
    210                 215                 220

Asn Asp Val Asp Ser Phe Glu Phe Tyr Leu His Thr Phe His Asp Val
225                 230                 235                 240

Leu Ile Gly Asn Asn Leu Phe Gly Arg Ser Ala Leu Lys Thr Ala Ala
                245                 250                 255

Glu Leu Ile Thr Lys Asp Glu Ile Lys Thr Ser Gly Ser Glu Ile Gly
            260                 265                 270

Lys Val Tyr Ser Phe Leu Ile Val Leu Thr Cys Leu Gln Ala Lys Ala
        275                 280                 285

Phe Leu Thr Leu Thr Ala Cys Arg Lys Leu Leu Gly Leu Ser Asp Ile
    290                 295                 300

Asp Tyr Thr Asn Ile Leu Asn Gln His Leu Asn Glu Lys Asn Val
305                 310                 315                 320

Phe Arg Asp Asn Ile Leu Pro Thr Leu Ser Asn Lys Phe Ser Asn Pro
                325                 330                 335

Asn Tyr Val Lys Thr Ile Gly Ser Asp Asn Tyr Ala Lys Val Ile Leu
            340                 345                 350

Glu Ala Glu Pro Gly Tyr Ala Leu Val Gly Phe Glu Ile Ile Asn Asp
        355                 360                 365

-continued

```
Pro Ile Pro Val Leu Lys Ala Tyr Gln Ala Lys Leu Lys Gln Asn Tyr
370                 375                 380

Gln Val Asp Asn Gln Ser Leu Ser Glu Ile Val Tyr Leu Asp Ile Asp
385                 390                 395                 400

Lys Leu Phe Cys Pro Lys Asn Ser Glu Gln Lys Tyr Tyr Thr Lys Ser
                405                 410                 415

Leu Thr Phe Pro Asp Gly Tyr Val Ile Thr Lys Ile Thr Phe Glu Lys
                420                 425                 430

Lys Leu Asn Asn Leu Arg Tyr Glu Ala Thr Ala Asn Phe Tyr Asp Pro
            435                 440                 445

Ser Thr Gly Ala Ile Asp Leu Asn Glu Lys Gln Val Glu Ser Thr Phe
450                 455                 460

Leu Lys Ala Asp Tyr Ile Ser Ile Asn Val Ser Asp Asp Asp Asp
465                 470                 475                 480

Gly Val Tyr Met Pro Leu Gly Val Ile Ser Glu Thr Phe Leu Ser Pro
                485                 490                 495

Ile Asn Ser Phe Glu Leu Glu Val Asp Glu Lys Ser Lys Ile Leu Thr
                500                 505                 510

Leu Thr Cys Lys Ser Tyr Leu Arg Glu Tyr Leu Leu Glu Ser Asp Leu
            515                 520                 525

Ile Asn Lys Glu Thr Ser Leu Ile Ala Pro Pro Asn Val Phe Ile Ser
530                 535                 540

Asn Ile Val Glu Asn Trp Asn Ile Glu Ala Asp Asn Leu Glu Pro Trp
545                 550                 555                 560

Val Ala Asn Asn Lys Asn Ala Tyr Val Asp Ser Thr Gly Gly Ile Glu
                565                 570                 575

Gly Ser Lys Ala Leu Phe Ala Gln Gly Asp Gly Glu Phe Ser Gln Phe
            580                 585                 590

Ile Gly Asp Lys Leu Lys Pro Asn Thr Asp Tyr Met Ile Gln Tyr Thr
                595                 600                 605

Val Lys Gly Lys Pro Ala Ile Tyr Leu Lys Asn Lys Asn Thr Gly Tyr
610                 615                 620

Thr Met Tyr Glu Asp Thr Asn Gly Ser Ser Glu Glu Phe Gln Thr Ile
625                 630                 635                 640

Ala Val Asn Tyr Thr Ser Glu Thr Asp Pro Ser Gln Thr His Leu Val
                645                 650                 655

Phe Lys Ser Gln Ser Gly Tyr Glu Ala Trp Gly Asp Asn Phe Ile Ile
                660                 665                 670

Leu Glu Ser Lys Ala Phe Glu Thr Pro Glu Gly Pro Glu Leu Ile Lys
            675                 680                 685

Phe Asp Asn Trp Thr Arg Ser Gly Gly Thr Phe Ile Ser Gly Asn Glu
690                 695                 700

Leu Val Ile Asn Ala Arg Asn Gly Asn Phe Arg Gln Asn Ile Gln Leu
705                 710                 715                 720

Gly Ser Phe Ser Thr Tyr Asn Met Ser Phe Ser Ile Arg Gly Ala Cys
                725                 730                 735

Arg Val Arg Ile Ser Asn Gln Gly Thr Thr Ile Phe Gln Gln Asp Tyr
                740                 745                 750

His Asp Thr Thr Tyr Ile Asn Ile Thr Glu Ser Phe Thr Lys Thr
            755                 760                 765

Ile Ser Ser Thr Ser Leu Ile Glu Phe Ser Ser Pro Asn Leu Ser Thr
770                 775                 780

Pro Tyr Asn Asn Ala Tyr Gly Arg Asp Phe Ser Ile Arg Glu Lys Ile
```

Glu Phe

<210> SEQ ID NO 5
<211> LENGTH: 2412
<212> TYPE: DNA
<213> ORGANISM: Artificial
<220> FEATURE:
<223> OTHER INFORMATION: Synthetic coding sequence used for expression
in a plant cell encoding TIC13085.

<400> SEQUENCE: 5

```
atgaagcaga acaacaacct cagcgtccgg gcgctcccag gcttcatcga cgtcttcaac      60
ggcatctacg gcttcgccac cggcatccag acatcatca acatgatctt ccggacggac     120
accggcgacc tcacgctgga ggaggtgctc aagaaccagg atctgctgaa ccacatcagc     180
gggaagctcg acggcatcaa cggcgacctc tccgagatca tcgcccaggg caacctgaac     240
accgagctgg cgaaggaact gctcaagatc gccaacgagc agaacaacgt cctcaccgac     300
gtgaacaaca agctgaacgc gatcaacgcg atgctgaaca cctacctgcc aagatcacg     360
aacatgctct cggacatcat gaagcagaac tacgtcctct cgctccagat cgagtacctg     420
tcgaagcagc tccaggagat cagcgataag ctggacgtga taaacctcaa cgtgctcatc     480
aactccacgc tcaccgagat caccccggcc taccagcgga tcaagtacgt caacgagaag     540
ttcgacgagc tgacgctcgc cacggagaaa accctccgcg ccaagcaagg gagcttcaac     600
gaggacgtct tcgacaacga cacccctggac aacctgaccg agctgaccga gttggccaag     660
tccgtcacca agaacgacgt tgactccttc gagttctacc tgcacaccctt tcacgacgtg     720
ctgatcggca caaacctgtt cggccgctcc gccctcaaga ccgcctcgga gctcatcacg     780
aaggacgaga tcaagacctc cgggtcggag atcggcaagg tttacagctt cctcatcgtg     840
ctgacctgcc tccaggcgaa ggcgttcctg acgctgaccg cgtgccgcaa gctgctcggg     900
ctgaccgaca ttgactacac gaacatcctg accagcacc tgaacgacga aaagaacgag     960
ttccgcgtga acatcctgcc gaccctcagc aacaagttca gcaaccccaa ctacgcgaag    1020
accatcggga gcgacaacta cgcgaaggtc acgctggagg ccgagccggg ctacgccctc    1080
gtcgggttcg agatcatcaa cgacccgatc cccgtcctca gggctacca ggccaagctc    1140
aaacagaact accaagttga caaccagtcg ctgtccggca tcgtgtactt caacatcgac    1200
aagctgctgt gcccgaacaa gtccgagcag aagtattaca ccaagtccct caccttcccc    1260
gacggctacg tcatcacgaa gatcacgttc gaaaagaagc tcaacaacct ccgctacgag    1320
gccaccgcca acttctacga ccccctccact gggatcatcg acctgaacaa gaagcaagtg    1380
gagtccacct tcctccagga agtacatc gggttaaacg ccagcgacga cggcgtgtac    1440
atgccactag gcgtcatcag cgagacgttc ctgtcgccga tcaacagctt cgagctggac    1500
gtcaacgaga gtccaagat cctgacgctg acctgcaaga gctacctgcg cgagtacctg    1560
ctggagaccg acctgataaa caaggagacc tccctgatcg tccgcccaa cttcagcaac    1620
atcgtggaga acggggacat ccgtgcggac agcctggagc cgtggaaggc caacaacaag    1680
aacgcctacg tggacatcac cggcgggtg aatgggagca aggccctcta cacctacggc    1740
gacggggagt tctcgcagtt catcggcgat aagttgaagc ccaagaccga ctacatcatc    1800
caatacaccg tgaaggggaa gccgccatc tacctcaagc acaagaacac gacgactac    1860
atcatgtacg aggacacgaa cggcaactac gaggacttcc agaccaagac ggtcaaatat    1920
```

```
acctccggca cggacccgag cccggcgcac ctcgtgttca gaaccagag cggctacgag     1980 gcgtggggcg acaagttcat catcctagag gcgaagctct tcgagacgcc cgagacgccc     2040
gagagccccg agcttatcaa gttcgacaac tggatcaagt cgggcaactc caacgagtca     2100
tggatcagcg gcgacacctt cgtgctctac aacccgaacg gctcgttccg ccagaacctc     2160
cagcttgaca gcttcagcac ctacaacctc agcttcagct tcagcggcat caggggcaag     2220
gtgaccatca gaacagccg ggaggtgctg ttcgagaagg agtacgttta tgagggcctg     2280
gggttccacg acaaaacgga gtccttcacc acggcgtcca caaggacgg cttctttatc     2340 gagctgacca ccacgacgta ctcgacccag aactcctttc gcaacttttc gatcaaggag     2400
aagctagagt ga                                                         2412

<210> SEQ ID NO 6
<211> LENGTH: 2409
<212> TYPE: DNA
<213> ORGANISM: Artificial
<220> FEATURE:
<223> OTHER INFORMATION: Synthetic coding sequence used for expression
      in a plant cell encoding TIC13087.

<400> SEQUENCE: 6
atgaagcaga acaacaacct gtcggtccgc gcgctgccga tctggatcga cgtcttcaac       60
gggatctacg gcttctcgac cggcatccag gacatcttca acatgatctt cgggacggac      120
accggcgacc tcacgctgga ggaggtgttg aagaaccagg acctcctcaa cgagatcagc      180
ggcaagctgg acggcatcaa cggcgacctg tccgagatca tcgcccaggg caacctgaac      240
acagagtcca caaggaact gctcaagatc gccaacgagc agaacaacct gctcacggac      300
gtgaacaaca agctgaacgc catcaacgcg atgctcaaca cctacctgcc caagatcacg      360
aacatgctga gcgacatcat gaagcagaac tacgtcctga gcctgcaact tgagtacctg      420
tccaagcagc tccaggagat cagcgacaag ctcgacgtca tcaacctcaa cgtcctcatc      480
aactccacgc tgaccgagat cacgcccgcg taccagcgga tcaagtacgt caacgagaag      540
ttcgacgacc tcacgctcgc cacggagaag acgctgcgtg cgaagcaagg cagcttcaac      600
gaggacatct tcgacaacga caccctggag aacctgacgg agctgacgga gctggcgaag      660
tccgtgacca agaacgacgt tgactctttc gagttctacc tccacacctt tcacgacgtg      720
ctgattggga caacctcttt cggccgctcg gcgctcaaga cggcggcgga gctgattact      780
aaggacgaga tcaagaccag cggctccgag atcgggaagg tgtactcgtt cctcatcgtg      840
ctgacctgcc tccaggcgaa ggcgttcctc accctcacgg cctgccggaa gctgctcggg      900
ctgtcggaca tcgactacac gaacatcctc aaccagcacc tcaacgagga agaacgtc       960 ttccgcgaca acatcctccc gaccctatcc aacaagttct ccaacccgaa ctacgtgaag      1020
accatcggct cggacaacta cgctaaggtc atcctagagg cggagcccgg ctacgcgctg      1080
gtgggcttcg agatcatcaa cgacccgatc ccggtgctga agcgtacca ggcgaagctc       1140 aagcaaaact accaagtgga caaccagagc ctgagcgaga tcgtgtacct ggacatcgac      1200
aagctgttct gccccaagaa cagcgagcag aagtattaca ccaagagcct cacgttcccc      1260
gacgggtacg tcatcaccaa gatcaccttc gaaaagaagc tcaacaacct gcgctacgag      1320
gccaccgcca acttctacga ccccagcacg ggcgcaatcg acctcaacga gaagcaagtg      1380
gagtcaacat tcctaaaggc cgactacatc tcgataaacg tgagcgacga cgacgacgat      1440
ggcgtgtaca tgccgctagg cgtgataagc gagacgttcc tgagcccgat caacagcttt      1500
```

```
gagcttgagg tggatgagaa gtccaagatc ctgaccctga cctgcaagag ctacctgcgg    1560
gagtacctcc ttgagagcga cctcatcaac aaggagacca gcctcatcgc cccgccgaac    1620
gtcttcatca gcaacatcgt cgagaactgg aacatcgagg ccgacaacct ggagccgtgg    1680
gtggccaaca acaagaacgc ctacgtggac tcgaccggcg gcatcgaggg cagcaaggcg    1740
ctcttcgccc agggcgacgg tgagttctcg cagttcatcg gggataagct caagccgaac    1800
acggactaca tgatccagta tacggtcaag ggcaagccag cgatctacct caagaacaag    1860
aacaccggct acacgatgta cgaggacacc aacgggtcga gcgaggagtt ccagaccatc    1920
gcggtcaact acacctcgga gaccgacccc tcccagaccc acctcgtgtt caagtcccag    1980
agcgggtacg aggcgtgggg cgacaacttc atcatcctgg agtctaaggc gttcgagacg    2040 ccggagggc cggagctgat taagttcgac aactggaccc gctccggcgg cacgttcatc    2100
agcggcaacg agctggtcat caacgcgcgg aacggcaact tccgccagaa catccagctc    2160
ggctccttct ccacgtacaa tatgtcgttc tccatccggg gcgcgtgccg cgtccgcatc    2220
tcgaaccagg gcaccaccat cttccaacag gactaccacg atacgaccta catcaacatc    2280
accgagagct tcaccacgaa gacgatctcc tccaccagcc tgatcgagtt cagcagcccg    2340
aacctgagca ccccgtacaa caacgcctac gggcgcgact tctcgattcg ggagaaaatc    2400
gagttctga                                                           2409
```

INSECT INHIBITORY PROTEINS

REFERENCE TO RELATED APPLICATION

This application claims the benefit of U.S. provisional application No. 63/132,877, filed Dec. 31, 2020, which is herein incorporated by reference in its entirety.

INCORPORATION OF SEQUENCE LISTING

The file named "MONS486US-sequence_listing.txt" containing a computer-readable form of the Sequence Listing was created on Dec. 9, 2021. This file is 27,917 bytes (measured in MS-Windows®), filed contemporaneously by electronic submission (using the United States Patent Office EFS-Web filing system), and incorporated by reference in its entirety.

FIELD OF THE INVENTION

The invention generally relates to the field of insect inhibitory proteins. A novel class of proteins are disclosed exhibiting insect inhibitory activity against agriculturally relevant pests of crop plants and seeds, particularly Lepidopteran species of insects. Plants, plant parts, and seeds, including plant and microbial cells, and vectors containing a recombinant polynucleotide construct encoding one or more of the disclosed toxin proteins are provided.

BACKGROUND OF THE INVENTION

Improving crop yield from agriculturally significant plants including, among others, corn, soybean, sugarcane, rice, wheat, vegetables, and cotton, has become increasingly important. In addition to the growing need for agricultural products to feed, clothe and provide energy for a growing human population, climate-related effects and pressure from the growing population to use land other than for agricultural practices are predicted to reduce the amount of arable land available for farming. These factors have led to grim forecasts of food security, particularly in the absence of major improvements in plant biotechnology and agronomic practices. In light of these pressures, environmentally sustainable improvements in technology, agricultural techniques, and pest management are vital tools to expand crop production on the limited amount of arable land available for farming.

Insects, particularly insects within the order Lepidoptera, are considered a major cause of damage to field crops, thereby decreasing crop yields over infested areas. Lepidopteran pest species which negatively impact agriculture include, but are not limited to, Black armyworm (*Spodoptera cosmioides*), Black cutworm (*Agrotis ipsilon*), Corn earworm (*Helicoverpa zea*), Cotton leaf worm (*Alabama argillacea*), Diamondback moth (*Plutella xylostella*), European corn borer (*Ostrinia nubilalis*), Fall armyworm (*Spodoptera frugiperda*), Cry1Fa1 resistant Fall armyworm (*Spodoptera frugiperda*), Old World bollworm (OWB, *Helicoverpa armigera*), Southern armyworm (*Spodoptera eridania*), Soybean looper (*Chrysodeixis includens*), Spotted bollworm (*Earias vittella*), Southwestern corn borer (*Diatraea grandiosella*), Sunflower looper (*Rachiplusia nu*), Tobacco budworm (*Heliothis virescens*), Tobacco cutworm (*Spodoptera litura*, also known as cluster caterpillar), Western bean cutworm (*Striacosta albicosta*), and Velvet bean caterpillar (VBC, *Anticarsia gemmatalis*).

Historically, the intensive application of synthetic chemical insecticides was relied upon as the pest control agent in agriculture. Concerns for the environment and human health, in addition to emerging resistance issues, stimulated the research and development of biological pesticides. This research effort led to the progressive discovery and use of various entomopathogenic microbial species, including bacteria.

The biological control paradigm shifted when the potential of entomopathogenic bacteria, especially bacteria belonging to the genus *Bacillus*, was discovered and developed as a biological pest control agent. Strains of the bacterium *Bacillus thuringiensis* (Bt) have been used as a source for pesticidal proteins since it was discovered that Bt strains show a high toxicity against specific insects. Bt strains are known to produce delta-endotoxins that are localized within parasporal crystalline inclusion bodies at the onset of sporulation and during the stationary growth phase (e.g., Cry proteins), and are also known to produce secreted insecticidal protein. Upon ingestion by a susceptible insect larvae, delta-endotoxins as well as secreted toxins exert their effects at the surface of the insect larvae midgut epithelium, disrupting the cell membrane, leading to cell disruption and death. Genes encoding insecticidal proteins have also been identified in bacterial species other than Bt, including other *Bacillus* and a diversity of additional bacterial species, such as *Brevibacillus laterosporus, Lysinibacillus sphaericus* ("Ls" formerly known as *Bacillus sphaericus*), *Paenibacillus popilliae* and *Paenibacillus lentimorbus*. In addition, insecticidal toxins have also been identified from a variety of non-bacterial sources including fungi, ferns, and arachnid venoms. Delivery of pesticidally effective amounts of such toxins in the diet of a pest is an effective way of controlling the target pest. For some susceptible pest species, pesticidally effective amounts of dsRNA specific for and targeting an essential gene for suppression has been identified as an effective pest management strategy, particularly when coupled with one or more pesticidal proteins.

Crystalline and soluble secreted insecticidal toxins are highly specific for intended target hosts and have gained worldwide acceptance and preferred as alternatives to chemical insecticides. For example, insecticidal toxin proteins have been employed in various agricultural applications to protect agriculturally important plant species from insect infestations, decrease the need for chemical pesticide applications, and increase yields. Insecticidal toxin proteins are used to control agriculturally-relevant pests of crop plants by mechanical methods, such as spraying to disperse microbial formulations containing various bacteria strains onto plant surfaces, and by using genetic transformation techniques to produce transgenic plants and seeds expressing insecticidal toxin protein(s).

The use of transgenic plants expressing insecticidal toxin proteins has been globally adapted. For example, in 2016, more than 23 million hectares were planted with transgenic crops expressing Bt toxins and more than 75 million hectares were planted with transgenic crops expressing Bt toxins stacked with herbicide tolerance traits (*ISAAA. 2016. Global Status of Commercialized Biotech/GM Crops: 2016. ISAAA Brief No. 52*. ISAAA: Ithaca, N.Y.). The global use of transgenic insect-protected crops and the limited number of insecticidal toxin proteins used in these crops has imposed pressure for selection of existing insect alleles that impart resistance to the currently-utilized insecticidal proteins.

The development of resistance to insecticidal toxin proteins in target pests creates the continuing need for discovery and development of new forms of insecticidal toxin proteins that are useful for managing the increase in insect resistance to transgenic crops expressing insecticidal toxin proteins. New protein toxins with improved efficacy and which exhibit control over a broader spectrum of susceptible insect species will reduce the number of surviving insects which can develop resistance alleles. In addition, the use in one plant of two or more transgenic insecticidal toxin proteins toxic to the same insect pest and displaying different modes of action or alternatively two or more different modes of toxic action (for example, a transgene encoding a dsRNA targeting an essential gene for suppression coupled with a transgene that encodes a peptide or protein toxin, both toxic to the same insect species) reduces the probability of, and the likelihood of development of, resistance in any single target insect species. Additionally, use of self-limiting technologies such as those provided by Oxitec Ltd, when used together with the proteins of the present invention, may improve durability of the insect resistance traits imparted to transgenic crops expressing proteins of the present invention (Zhou et al. 2018. *Evol Appl* 11(5):727-738; Alphey et al. 2009. *Journal of Economic Entomology*, 102: 717-732).

Thus, the inventors disclose herein, novel proteins derived from *Bacillus thuringiensis* species, along with engineered variant proteins, and exemplary recombinant proteins, that each exhibit insecticidal activity against target Lepidopteran species, such as against Black cutworm (*Agrotis ipsilon*), Corn earworm (*Helicoverpa zea*), European corn borer (*Ostrinia nubilalis*), Fall armyworm (*Spodoptera frugiperda*), Southern armyworm (*Spodoptera eridania*), Southwestern corn borer (*Diatraea grandiosella*), and Soybean looper (*Chrysodeixis includens*).

SUMMARY OF THE INVENTION

Disclosed herein are novel pesticidal proteins, TIC13085 and TIC13087, which are shown to exhibit inhibitory activity against one or more pests of crop plants. The TIC13085 and TIC13087 proteins can be used alone or in combination with other insecticidal proteins and toxic agents in formulations and in planta, thus providing alternatives to insecticidal proteins and insecticide chemistries currently in use in agricultural systems.

In one embodiment is a recombinant nucleic acid molecule comprising a heterologous promoter operably linked to a polynucleotide segment encoding a pesticidal protein or pesticidal fragment thereof, wherein the pesticidal protein comprises the amino acid sequence as set forth in SEQ ID NO:2 or SEQ ID NO:4. The pesticidal protein comprises an amino acid sequence having at least 88%, or 90%, or 95%, or 98% or 99%, or about 100% amino acid sequence identity to the amino acid sequence as set forth in SEQ ID NO:2 or SEQ ID NO:4. The polynucleotide segment encoding the protein hybridizes under stringent hybridization conditions to a polynucleotide having the nucleotide sequence as set forth in SEQ ID NO:1, SEQ ID NO:3, SEQ ID NO:5, or SEQ ID NO:6. The recombinant nucleic acid molecule is a nucleotide sequence that encodes the pesticidal protein and can be expressed in a plant cell, and which when expressed in a plant cell produces a pesticidally effective amount of pesticidal protein or a pesticidal fragment thereof.

In another embodiment the recombinant nucleic acid molecule is present within a bacterial or plant host cell. Contemplated bacterial host cells include at least the genus of *Agrobacterium, Rhizobium, Bacillus, Brevibacillus, Escherichia, Pseudomonas, Klebsiella, Pantoea*, and *Erwinia*. In certain embodiments, the *Bacillus* species is a *Bacillus cereus* or *Bacillus thuringiensis*, the *Brevibacillus* is a *Brevibacillus laterosporus*, or the *Escherichia* species is *Escherichia coli*. Contemplated plant host cells include a dicotyledonous plant cells and a monocotyledonous plant cells. Contemplated plant cells further may include an alfalfa, banana, barley, bean, broccoli, cabbage, brassica (including mustard and canola), carrot, cassava, castor, cauliflower, celery, chickpea, Chinese cabbage, citrus, coco nut, coffee, corn (including sweet corn and field corn), clover, cotton (*Gossypium* sp.), a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, Radiata pine, radish, rapeseed (canola), rice, rootstocks, rye, safflower, shrub, sorghum, Southern pine, soybean, spinach, squash, strawberry, sugar beet, sugarcane, sunflower, sweet gum, sweet potato, switchgrass, tea, tobacco, tomato, triticale, turf grass, watermelon, and wheat plant cells.

In another embodiment, the pesticidal protein exhibits activity against Lepidopteran insects, including, at least, Black cutworm (*Agrotis ipsilon*), Corn earworm (*Helicoverpa zea*), European corn borer (*Ostrinia nubilalis*), Fall armyworm (*Spodoptera frugiperda*), Southern armyworm (*Spodoptera eridania*), Southwestern corn borer (*Diatraea grandiosella*), and Soybean looper (*Chrysodeixis includens*).

Also contemplated in this application are bacteria and plants and plant parts comprising a recombinant nucleic acid molecule encoding a pesticidally effective amount of the pesticidal protein TIC13085 or TIC13087 or pesticidal fragments thereof. The recombinant molecule (e.g. construct) may comprise a heterologous promoter for expression in bacterial or plant cells of the operably linked polynucleotide segment encoding the pesticidal protein. Both dicotyledonous plants and monocotyledonous plants are contemplated. In another embodiment, the plant is further selected from the group consisting of an alfalfa, banana, barley, bean, broccoli, cabbage, brassica (e.g. canola or rapeseed), carrot, cassava, castor, cauliflower, celery, chickpea, Chinese cabbage, citrus, coconut, coffee, corn (maize, including sweet corn and field corn), clover, cotton (i.e. *Gossypium* sp.), a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeon pea, pine, potato, poplar, pumpkin, Radiata pine, radish, rice, rootstocks, rye, safflower, shrub, sorghum, Southern pine, soybean, spinach, squash, strawberry, sugar beet, sugarcane, sunflower, sweet gum, sweet potato, switchgrass, tea, tobacco, tomato, triticale, turf grass, watermelon, and wheat plants. The plant parts may for instance include, without limitation, leaves, tubers, roots, stems, seeds, embryos, flowers, inflorescences, bolls, pollen, fruit, animal feed, and biomass. Processed plant parts, for instance wood, or oil, non-viable ground seeds or fractionated seeds, flour, or starch produced from the plant leaves, flowers, roots, seeds or tubers are also contemplated.

In certain embodiments, seeds comprising the recombinant nucleic acid molecules are disclosed.

In still another embodiment, an insect inhibitory composition comprising the recombinant nucleic acid molecules disclosed in this application are contemplated. The insect inhibitory composition can further comprise a nucleotide sequence encoding at least one other pesticidal agent that is different from the pesticidal protein of the present invention. In certain embodiments, the other pesticidal agent is selected from the group consisting of an insect inhibitory protein, an insect inhibitory dsRNA molecule, and an ancillary protein. It is also contemplated that the other pesticidal agent in the insect inhibitory composition exhibits activity against one or more pest species of the orders Lepidoptera, Coleoptera, or Hemiptera. The other pesticidal agent in the insect inhibitory composition may be an embodiment selected from the group consisting of a Cry1A, Cry1Ab, Cry1Ac, Cry1A.105, Cry1Ae, Cry1B, Cry1C, Cry1C variants, Cry1D, Cry1E, Cry1F, Cry1A/F chimeras, Cry1G, Cry1H, Cry1I, Cry1J, Cry1K, Cry1L, Cry2A, Cry2Ab, Cry2Ae, Cry3, Cry3A variants, Cry3B, Cry4B, Cry6, Cry7, Cry8, Cry9, Cry15, Cry34, Cry35, Cry43A, Cry43B, Cry51Aa1, ET29, ET33, ET34, ET35, ET66, ET70, TIC400, TIC407, TIC417, TIC431, TIC800, TIC807, TIC834, TIC853, TIC900, TIC901, TIC1201, TIC1415, TIC2160, TIC3131, TIC836, TIC860, TIC867, TIC869, TIC1100, VIP3A, VIP3B, VIP3Ab, AXMI-88, AXMI-97, AXMI-102, AXMI-112, AXMI-117, AXMI-100, AXMI-115, AXMI-113, and AXMI-005, AXMI134, AXMI-150, AXMI-171, AXMI-184, AXMI-196, AXMI-204, AXMI-207, AXMI-209, AXMI-205, AXMI-218, AXMI-220, AXMI-221z, AXMI-222z, AXMI-223z, AXMI-224z and AXMI-225z, AXMI-238, AXMI-270, AXMI-279, AXMI-345, AXMI-335, AXMI-R1, and pesticidal variants thereof of the foregoing, IP3 and variants thereof, DIG-3, DIG-5, DIG-10, DIG-657, DIG-11 protein, IDP102Aa and homologs thereof, IDP110Aa and homologs thereof, TIC868, Cry1Da1_7, BCW003, TIC1100, TIC867, TIC867_23, TIC6757, TIC7941, IDP072Aa, TIC5290, TIC3668, TIC3669, TIC3670, TIC4029, TIC4064, IDP103 and homologs thereof, PIP-50 and PIP-65 and homologs thereof, PIP-83 and homologs thereof, and Cry1B.34.

Commodity products comprising a detectable amount of the recombinant nucleic acid molecules and/or toxin proteins of the present invention are also contemplated. Such commodity products include commodity corn bagged by a grain handler, corn flakes, corn cakes, corn flour, corn meal, corn syrup, corn oil, corn silage, corn starch, corn cereal, and the like, and corresponding soybean, rice, wheat, sorghum, pigeon pea, peanut, fruit, melon, and vegetable commodity products including, where applicable, juices, concentrates, jams, jellies, marmalades, and other edible forms of such commodity products containing a detectable amount of such polynucleotides and or polypeptides of the present invention, whole or processed cotton seed, cotton oil, lint, seeds and plant parts processed for feed or food, fiber, paper, biomasses, and fuel products such as fuel derived from cotton oil or pellets derived from cotton gin waste, whole or processed soybean seed, soybean oil, soybean protein, soybean meal, soybean flour, soybean flakes, soybean bran, soybean milk, soybean cheese, soybean wine, animal feed comprising soybean, paper comprising soybean, cream comprising soybean, soybean biomass, and fuel products produced using soybean plants and soybean plant parts.

Also contemplated in this application is a method of producing seed comprising recombinant nucleic acid molecules encoding the TIC13085 and TIC13087 toxin proteins. The method comprises planting at least one seed comprising a recombinant nucleic acid molecule encoding the TIC13085 or TIC13087 toxin; growing a plant from the seed; and harvesting seed from the plant, wherein the harvested seed comprises the referenced recombinant nucleic acid molecule encoding the applicable toxin.

In another embodiment, a plant resistant to Lepidopteran insect infestation is provided in which the cells of the plant contain the recombinant nucleic acid molecule described herein and which encodes a TIC13085 or TIC13087 toxin.

Also disclosed in this application are methods for controlling a Lepidopteran species pest and controlling a Lepidopteran species pest infestation of a plant, particularly a crop plant. The method comprises, in one embodiment, first contacting the pest with an insecticidally effective amount of a pesticidal protein having the amino acid sequence as set forth in SEQ ID NO:2 or SEQ ID NO:4; or contacting the pest with an insecticidally effective amount of one or more such pesticidal proteins and which are composed of an amino acid sequence having at least 88%, or 90%, or 95%, or 98% or 99%, or about 100% amino acid sequence identity to the amino acid sequence as set forth in SEQ ID NO:2 or SEQ ID NO:4.

Further provided herein is a method of detecting the presence of a recombinant nucleic acid molecule encoding the TIC13085 and TIC13087 toxin protein class, wherein the method comprises contacting a sample of nucleic acids with a nucleic acid probe that hybridizes under stringent hybridization conditions with genomic DNA from a plant comprising a polynucleotide segment encoding a pesticidal protein or fragment thereof provided herein. The probe does not hybridize under such hybridization conditions with genomic DNA from an otherwise isogenic plant that does not contain the polynucleotide segment, and the probe is homologous or complementary to the nucleotide sequence as set forth in SEQ ID NO:5 or SEQ ID NO:6. The probe may also hybridize to a polynucleotide segment that encodes a pesticidal protein comprising at least 88%, or 90%, or 95%, or 98% or 99%, or about 100% amino acid sequence identity to the amino acid sequence as set forth in SEQ ID NO:2 or SEQ ID NO:4. The method further provides for subjecting the sample and probe to stringent hybridization conditions, and detecting hybridization of the probe with DNA (or other polynucleotide segment such as mRNA) of the sample. In some embodiments a step of detecting the presence of a member of the TIC13085 or TIC13087 toxin protein class may comprise an ELISA or a western blot in which antibodies that recognize epitopes of TIC13085 or TIC13087 also recognize and bind to similar or identical epitopes of a member of this protein class but in a protein having an amino acid sequence that is altogether different from that of the proteins disclosed herein.

Also provided herein are methods of detecting the presence of the pesticidal protein or pesticidal/insecticidal fragment thereof from the TIC13085 and TIC13087 toxin protein class wherein the method comprises contacting a biological sample with a TIC13085 and TIC13087 toxin protein class immunoreactive antibody and detecting the binding of the antibody to the TIC13085 and TIC13087 toxin protein class protein in the sample, thus confirming the presence of the related protein in the sample. In some embodiments the step of detecting comprises an ELISA, or a Western blot.

Also contemplated is a method for controlling a Lepidopteran pest species or pest infestation in a field wherein the method comprises planting a crop seed which contains a recombinant nucleotide sequence within its genome that encodes a toxin protein similar or related to the TIC13085 or TIC13087 toxin proteins or toxic fragments thereof, and growing a transgenic/recombinant crop plant which expresses in its cells an insecticidally effective amount of a pesticidal protein having the amino acid sequence as set forth in SEQ ID NO:2 or SEQ ID NO:4 or growing a crop plant which expresses an insecticidally effective amount of one or more pesticidal proteins, provided that at least one of the pesticidal proteins has an amino acid sequence having at least 88%, or 90%, or 95%, or 98% or 99%, or about 100% amino acid sequence identity to the amino acid sequence as set forth in SEQ ID NO:2 or SEQ ID NO:4; and optionally releasing into or near the field, one or more transgenic Lepidopteran pest species each carrying a self-limiting gene, for the purpose of preventing or delaying the onset of resistance of the one or more Lepidopteran pest species to the toxin protein. In one embodiment, the crop plants can be monocotyledonous or dicotyledonous. In another embodiment, the monocotyledonous crop plants can be corn, wheat, sorghum, rice, rye, or millet. In yet another embodiment, the dicotyledonous crop plant can be soybean, cotton, or canola.

BRIEF DESCRIPTION OF THE SEQUENCES

SEQ ID NO:1 is a nucleic acid sequence encoding a TIC13085 pesticidal protein obtained from *Bacillus thuringiensis*.

SEQ ID NO:2 is the amino acid sequence of the TIC13085 pesticidal protein.

SEQ ID NO:3 is a nucleic acid sequence encoding a TIC13087 pesticidal protein obtained from *Bacillus thuringiensis*.

SEQ ID NO:4 is the amino acid sequence of the TIC13087 pesticidal protein.

SEQ ID NO:5 is a synthetic coding sequence used for expression in a plant cell encoding TIC13085.

SEQ ID NO:6 is a synthetic coding sequence used for expression in a plant cell encoding TIC13087.

DETAILED DESCRIPTION OF THE INVENTION

One problem in the art of agricultural pest control can be characterized as a need for new toxin proteins that are efficacious against target pests, exhibit broad spectrum toxicity against target pest species, are capable of being expressed in plants without causing undesirable agronomic issues, and provide an alternative mode of action compared to current toxins that are used commercially in plants.

Novel pesticidal proteins exemplified by TIC13085 and TIC13087 are disclosed herein, and address each of these problems in the art, particularly against a broad spectrum of Lepidopteran insect pests, such as against Black cutworm (*Agrotis ipsilon*), Corn earworm (*Helicoverpa zea*), European corn borer (*Ostrinia nubilalis*), Fall armyworm (*Spodoptera frugiperda*), Southern armyworm (*Spodoptera eridania*), Southwestern corn borer (*Diatraea grandiosella*), and Soybean looper (*Chrysodeixis includens*).

Reference in this application to TIC13085, "TIC13085 protein", "TIC13085 protein toxin", "TIC13085 pesticidal protein", "TIC13085-related toxins", "TIC13085-related toxins", "TIC13085 protein toxin class", "TIC13085 toxin protein class" and the like, refer to any novel pesticidal protein or insect inhibitory protein, that comprises, that consists of, that is substantially homologous to, that is similar to, or that is derived from any pesticidal protein or insect inhibitory protein having the amino acid sequence as set forth in TIC13085 (SEQ ID NO:2), and pesticidal or insect inhibitory segments thereof, or combinations thereof, that confer activity against Lepidopteran pests, including any protein exhibiting pesticidal or insect inhibitory activity if alignment of such protein with TIC13085 results in an amino acid sequence identity of any fraction percentage from about 88% to about 100% percent. The TIC13085 proteins include both the plastid-targeted and non-plastid targeted form of the proteins.

Reference to this application to TIC13087, "TIC13087 protein", "TIC13087 protein toxin", "TIC13087 pesticidal protein", "TIC13087-related toxins, "TIC13087-related toxins", "TIC13087 protein toxin class", "TIC13087 toxin protein class" and the like, refer to any novel pesticidal protein or insect inhibitory protein, that comprises, that consists of, that is substantially homologous to, that is similar to, or that is derived from any pesticidal protein or insect inhibitory protein having the amino acid sequence as set forth in TIC13087 (SEQ ID NO:4), and pesticidal or insect inhibitory fragments or segments thereof, or combinations thereof, that confer activity against Lepidopteran pests, including any protein exhibiting pesticidal or insect inhibitory activity, if alignment of such amino acid sequence with the amino acid sequence of TIC13087 results in an amino acid sequence identity of any fraction percentage from about 88% to about 100% percent. The TIC13087 proteins include both the plastid-targeted and non-plastid targeted form of the proteins.

The term "segment" or "fragment" is used in this application to describe consecutive amino acid or nucleic acid sequences that are shorter than the complete amino acid or nucleic acid sequence descriptive of a TIC13085 or TIC13087 coding sequence or protein. A segment or fragment exhibiting insect inhibitory activity is also disclosed in this application if alignment of such segment or fragment, with the corresponding section of the TIC13085 protein set forth in SEQ ID NO:2 or the TIC13087 protein set forth in SEQ ID NO:4, results in amino acid sequence identity of any fraction percentage from about 85% or about 88% to about 100% between the segment or fragment and the corresponding segment of amino acids within the TIC13085 or TIC13087 proteins. A fragment as described herein may comprise at least 50, at least 100, at least 250, at least 400, at least 500, at least 600, or at least 800 contiguous amino acid residues of the TIC13085 or TIC13087 proteins.

Reference in this application to the terms "active" or "activity", "pesticidal activity" or "pesticidal" or "insecticidal activity", "insect inhibitory", "pesticidally effective" or "insecticidal" refer to efficacy of a toxic agent, such as a protein toxin, in inhibiting (inhibiting growth, feeding, fecundity, or viability), suppressing (suppressing growth, feeding, fecundity, or viability), controlling (controlling the pest infestation, controlling the pest feeding activities on a particular crop) containing an effective amount of the TIC13085 or TIC13087 proteins or killing (causing the morbidity, mortality, or reduced fecundity of) a pest. These terms are intended to include the result of providing a pesticidally effective amount of a protein toxic to a pest where the exposure of the pest to the toxic protein results in morbidity, mortality, reduced fecundity, or stunting. These terms also include repulsion of the pest from the plant, a tissue of the plant, a plant part, seed, plant cells, or from the particular geographic location where the plant may be growing, as a result of providing a pesticidally effective amount of the toxic protein in or on the plant. In general, pesticidal activity refers to the ability of a toxic protein to be effective in inhibiting the growth, development, viability, feeding behavior, mating behavior, fecundity, or any measurable decrease in the adverse effects caused by an insect feeding. The toxic protein can be produced by the plant or can be applied to the plant or to the environment within the location where the plant is located. The terms "bioactivity", "effective", "efficacious" or variations thereof are also terms interchangeably utilized in this application to describe the effects of proteins of the present invention on target insect pests.

A pesticidally effective amount of a toxic agent, when provided in the diet of a target pest, exhibits pesticidal activity when the toxic agent contacts the pest. A toxic agent can be a pesticidal protein or one or more chemical agents known in the art. Pesticidal or insecticidal chemical agents can be used alone or in combinations with each other. Chemical agents include but are not limited to dsRNA molecules targeting specific genes for suppression in a target pest, organochlorides, organophosphates, carbamates, pyrethroids, neonicotinoids, and ryanoids. Pesticidal or insecticidal protein agents include the protein toxins set forth in this application, as well as other proteinaceous toxic agents including those that target Lepidopterans, as well as protein toxins that are used to control other plant pests such as Cry, Vip, and Cyt proteins available in the art for use in controlling Coleopteran, Hemipteran and Homopteran species.

It is intended that reference to a pest, particularly a pest of a crop plant, means insect pests of crop plants, particularly those Lepidoptera insect pests that are controlled by the TIC13085 or TIC13087 protein toxin class. However, reference to a pest can also include Coleopteran, Hemipteran and Homopteran insect pests of plants, as well as nematodes and fungi when toxic agents targeting these pests are co-localized or present together with the TIC13085 or TIC13087 proteins or a protein that is 85 to about 100 percent identical to TIC13085 or TIC13087 proteins. The phrases "present together" or "co-localized" are intended to include any instance of which a target insect pest has been contacted by a TIC13085 or TIC13087 toxin protein as well as any other toxic agent also present in a pesticidally effective amount relative to the target insect pest. "Contacted" is intended in certain embodiments to refer to being present in the diet of the target pest, and the diet is consumed by the target pest.

The TIC13085 and TIC13087 proteins are related by a common function and exhibit insecticidal activity towards insect pests from the Lepidoptera insect species, including adults, pupae, larvae, and neonates.

The insects of the order Lepidoptera include, but are not limited to, armyworms, cutworms, loopers, and heliothines in the Family Noctuidae, e.g., Fall armyworm (*Spodoptera frugiperda*), Bean shoot moth (*Crocidosema aporema*), Beet armyworm (*Spodoptera exigua*), Black armyworm (*Spodoptera cosmioides*), Southern armyworm (*Spodoptera eridania*), bertha armyworm (*Mamestra configurata*), black cutworm (*Agrotis ipsilon*), cabbage looper (*Trichoplusia ni*), soybean looper (*Pseudoplusia includens*), Sunflower looper (*Rachiplusia nu*), velvetbean caterpillar (*Anticarsia gemmatalis*), green cloverworm (*Hypena scabra*), tobacco budworm (*Heliothis virescens*), granulate cutworm (*Agrotis subterranea*), armyworm (*Pseudaletia unipuncta*), Sunflower looper (*Rachiplusia nu*), South American podworm (*Helicoverpa gelotopoeon*) western cutworm (*Agrotis orthogonia*); borers, casebearers, webworms, coneworms, cabbageworms and skeletonizers from the Family Pyralidae, e.g., European corn borer (*Ostrinia nubilalis*), navel orange worm (*Amyelois transitella*), corn root webworm (*Crambus caliginosellus*), sod webworm (*Herpetogramma licarsisalis*), sunflower moth (*Homoeosoma electellum*), lesser cornstalk borer (*Elasmopalpus lignosellus*); leafrollers, budworms, seed worms, and fruit worms in the Family Tortricidae, e.g., codling moth (*Cydia pomonella*), grape berry moth (*Endopiza viteana*), oriental fruit moth (*Grapholita molesta*), sunflower bud moth (*Suleima helianthana*); and many other economically important Lepidoptera, e.g., diamondback moth (*Plutella xylostella*), pink bollworm (*Pectinophora gossypiella*), and gypsy moth (*Lymantria dispar*). Other insect pests within the order Lepidoptera include, e.g., cotton leaf worm (*Alabama argillacea*), fruit tree leaf roller (*Archips argyrospila*), European leafroller (*Archips rosana*) and other *Archips* species, (*Chilo suppressalis*, Asiatic rice borer, or rice stem borer), rice leaf roller (*Cnaphalocrocis medinalis*), corn root webworm (*Crambus caliginosellus*), bluegrass webworm (*Crambus teterrellus*), southwestern corn borer (*Diatraea grandiosella*), sugarcane borer (*Diatraea saccharalis*), spiny bollworm (*Earias insulana*), spotted bollworm (*Earias vittella*), American bollworm (*Helicoverpa armigera*), corn earworm (*Helicoverpa zea*, also known as soybean podworm and cotton bollworm), tobacco budworm (*Heliothis virescens*), sod webworm (*Herpetogramma licarsisalis*), Western bean cutworm (*Striacosta albicosta*), European grape vine moth (*Lobesia botrana*), citrus leafminer (*Phyllocnistis citrella*), large white butterfly (*Pieris brassicae*), small white butterfly (*Pieris rapae*, also known as imported cabbageworm), beet armyworm (*Spodoptera exigua*), tobacco cutworm (*Spodoptera litura*, also known as cluster caterpillar), and tomato leaf miner (*Tuta absoluta*).

Reference in this application to an "isolated DNA molecule", or an equivalent term or phrase, is intended to mean that the DNA molecule is one that is present alone or in combination with other compositions, but not within its natural environment. For example, nucleic acid elements such as a coding sequence, intron sequence, untranslated leader sequence, promoter sequence, transcriptional termination sequence, and the like, that are naturally found within the DNA of the genome of an organism are not considered to be "isolated" so long as the element is within the genome of the organism and at the location within the genome in which it is naturally found. However, each of these elements, and subparts of these elements, would be "isolated" within the scope of this disclosure so long as the element is not within the genome of the organism and at the location within the genome in which it is naturally found. Similarly, a nucleotide sequence encoding an insecticidal protein or any naturally occurring insecticidal variant of that protein would be an isolated nucleotide sequence so long as the nucleotide sequence was not within the DNA of the bacterium from which the sequence encoding the protein is naturally found. A synthetic nucleotide sequence encoding the amino acid sequence of the naturally occurring insecticidal protein would be considered to be isolated for the purposes of this disclosure. For the purposes of this disclosure, any transgenic nucleotide sequence, i.e., the nucleotide sequence of the DNA inserted into the genome of the cells of a plant or bacterium, or present in an extrachromosomal vector, would be considered to be an isolated nucleotide sequence whether it is present within the plasmid or similar structure used to transform the cells, within the genome of the plant or bacterium, or present in detectable amounts in tissues, progeny, biological samples or commodity products derived from the plant or bacterium.

Reference in this application to the term "self-limiting gene" refers to a gene that limits survival of the host, resulting in a reduction in the host population. Such technology is offered, for example, by Oxitech Ltd. Transgenic male insects carrying a transgenic self-limiting gene are released and reproduce with wild females. As a result, the progeny inherit a copy of the self-limiting gene. For example, the self-limiting Diamondback Moth (*Plutella xylostella*) strain OX4319L developed by Oxitech Ltd carries a male-selecting gene that utilizes sequences from the sex determination gene doublesex (dsx). The gene expresses sex-alternate splicing, resulting in female-specific expression of the self-limiting gene which prevents survival of female offspring beyond the larval stage and allows for production of male only cohorts of self-limiting moths. After being released, males mate with naturally occurring wild type females, leading to a reduction in the number of female offspring in the next generation, thereby locally suppressing *P. xylostella* populations. To facilitate the rearing of large numbers of males for release within diamondback moth production facilities, the expression of female-specific dsx within the OX4319L strain is repressed by the addition of tetracycline, or suitable analogs, into the larval feed. OX4319L also expresses the fluorescent protein, DsRed, which permits the monitoring of the presence of this strain in the field (Jin et al., 2013. Engineered female-specific lethality for control of pest Lepidoptera. ACS Synthetic Biology, 2: 160-166). This technology, when applied in the field with plants containing the toxin genes of the present invention, can delay or prevent the onset of resistance of pest species targeted for control by the toxin genes and proteins of the present invention, thus giving a greater durability of any plant product containing the toxin genes and proteins of the present invention.

As described further in this application, an open reading frame (ORF) encoding TIC13085 (SEQ ID NO:1) was discovered in DNA obtained from *Bacillus thuringiensis* isolated from soil in a wheat field in Genessee, Idaho as part of a metagenome sequencing effort using plate scrapes of bacteria grown from soil samples. The coding sequence was cloned and expressed in microbial host cells to produce recombinant protein used in bioassays. Bioassay using recombinant microbial host cell-derived TIC13085 protein demonstrated activity against the Lepidopteran species Fall armyworm (FAW, *Spodoptera frugiperda*), Soybean looper (SBL, *Chrysodeixis includens*), and Southwestern corn borer (SWC, *Diatraea grandiosella*). Also described further in this application, an open reading frame (ORF) encoding TIC13087 (SEQ ID NO:3) toxin protein was discovered in DNA obtained from *Bacillus thuringiensis* isolated from soil in a wheat field in Ashley, N. Dak. as part of a metagenome sequencing effort using plate scrapes of bacteria derived from the soil. Bioassay using recombinant microbial host cell-derived TIC13087 protein demonstrated activity against the Lepidopteran species Black cutworm (BCW, *Agrotis ipsilon*), Corn earworm (CEW, *Helicoverpa zea*), and Southwestern corn borer (SWC, *Diatraea grandiosella*).

Synthetic coding sequences designed for use in a plant cell were produced to express TIC13085 (SEQ ID NO:5) and TIC13087 (SEQ ID NO:6). Soybean plants expressing TIC13085 demonstrated activity against the Lepidopteran species Fall armyworm (FAW, *Spodoptera frugiperda*), Southern armyworm (SAW, *Spodoptera eridania*), and Soybean looper (SBL, *Chrysodeixis includens*). Soybean plants expressing TIC13087 demonstrated activity against the Lepidopteran species Corn earworm (CEW, *Helicoverpa zea*), also known as Soybean Pod Worm (SPW). Corn plants expressing TIC13085 demonstrated activity against the Lepidopteran species European corn borer (ECB, *Ostrinia nubilalis*), Fall armyworm (FAW, *Spodoptera frugiperda*), and Southwestern corn borer (SWC, *Diatraea grandiosella*). Corn plants expressing TIC13087 demonstrated activity against the Lepidopteran species Corn earworm (CEW, *Helicoverpa zea*), European corn borer (ECB, *Ostrinia nubilalis*), and Southwestern corn borer (SWC, *Diatraea grandiosella*).

For expression in plant cells, the TIC13085 (SEQ ID NO:2) and TIC13087 (SEQ ID NO:4) proteins can be expressed to reside in the cytosol or targeted to various subcellular organelles within the plant cell. For example, targeting a protein to the chloroplast or plastid may result in increased levels of expressed protein in a transgenic plant while preventing off-phenotypes from occurring. Targeting may also result in an increase in pest resistance efficacy in the transgenic event. A target peptide or transit peptide is a short (3-70 amino acids long) peptide chain that directs the transport of a protein to a specific region in the cell, including the nucleus, mitochondria, endoplasmic reticulum (ER), chloroplast, apoplast, peroxisome and plasma membrane. Some target peptides are cleaved from the protein by signal peptidases after the proteins are transported (or imported) into the applicable organelle. For targeting to the chloroplast, proteins contain transit peptides which are around 40-50 amino acids. For descriptions of the use of chloroplast transit peptides, see U.S. Pat. Nos. 5,188,642 and 5,728,925. Many chloroplast-localized proteins are expressed from nuclear genes as precursors and are targeted to the chloroplast by an N-terminal positioned chloroplast transit peptide (CTP). Examples of such isolated CTPs include, but are not limited to, those associated with the small subunit (SSU) of ribulose-1,5-bisphosphate carboxylase, ferredoxin, ferredoxin oxidoreductase, the light-harvesting complex protein I and protein II, thioredoxin F, enolpyruvyl shikimate phosphate synthase (EPSPS), and transit peptides described in U.S. Pat. No. 7,193,133. It has been demonstrated in vivo and in vitro that non-chloroplast proteins may be targeted to the chloroplast by use of protein fusions with a heterologous CTP and that the CTP is sufficient to target a protein to the chloroplast. Incorporation of a suitable chloroplast transit peptide such as the *Arabidopsis thaliana* EPSPS CTP (CTP2) (see, Klee et al., *Mol. Gen. Genet.* 210:437-442, 1987) or the *Petunia hybrida* EPSPS CTP (CTP4) (see, della-Cioppa et al., *Proc. Natl. Acad. Sci. USA* 83:6873-6877, 1986) has been shown to target heterologous EPSPS protein sequences to chloroplasts in transgenic plants (see, U.S. Pat. Nos. 5,627,061; 5,633, 435; and 5,312,910; and EP 0218571; EP 189707; EP 508909; and EP 924299). For targeting the TIC13085 or TIC13087 toxin protein to the chloroplast, a sequence encoding a chloroplast transit peptide is placed 5' in operable linkage and in frame to a synthetic coding sequence encoding the TIC13085 or TIC13087 toxin protein that has been designed for expression in plant cells.

It is contemplated that additional toxin protein sequences related to TIC13085 and TIC13087 can be created using the amino acid sequence of TIC13085 and TIC13087 to create novel proteins with novel properties. The TIC13085 and TIC13087 toxin proteins can be aligned to combine differences at the amino acid sequence level into novel amino acid sequence variants and making appropriate changes to the recombinant nucleic acid sequence encoding the variants.

This disclosure further contemplates that improved variants of the TIC13085 and TIC13087 protein toxin class can be engineered in planta by using various gene editing methods known in the art. Such technologies used for genome editing include, but are not limited to, ZFN (zinc-finger nuclease), mega-nucleases, TALEN (Transcription activator-like effector nucleases), and CRISPR (Clustered Regularly Interspaced Short Palindromic Repeats)/Cas (CRISPR-associated) systems. These genome editing methods can be used to alter the toxin protein coding sequence transformed within a plant cell to a different toxin coding sequence. Specifically, through these methods, one or more codons within the toxin coding sequence is altered to engineer a new protein amino acid sequence. Alternatively, a fragment within the coding sequence is replaced or deleted, or additional DNA fragments are inserted into the coding sequence, to engineer a new toxin coding sequence. The new coding sequence can encode a toxin protein with new properties such as increased activity or spectrum against insect pests, as well as provide activity against an insect pest species wherein resistance has developed against the original insect toxin protein. The plant cell comprising the gene edited toxin coding sequence can be used by methods known in the art to generate whole plants expressing the new toxin protein.

It is also contemplated that fragments of TIC13085 or TIC13087 or protein variants thereof can be truncated forms wherein one or more amino acids are deleted from the N-terminal end, C-terminal end, the middle of the protein, or combinations thereof wherein the fragments and variants retain insect inhibitory activity. These fragments can be naturally occurring or synthetic variants of TIC13085 or TIC13087 or derived protein variants but should retain the insect inhibitory activity of at least TIC13085 or TIC13087 full length toxin protein.

TABLE 1

Pair-wise matrix display of exemplary TIC13085 and TIC13087 protein.

| Toxin & (SEQ ID NO) | TIC13085 SEQ ID NO 2 | TIC13087 SEQ ID NO 4 |
|---|---|---|
| TIC13085 SEQ ID NO 2 | — | 82.6 (663) |
| TIC13087 SEQ ID NO 4 | 82.7 (663) | — |

In addition to percent amino acid sequence identity, TIC13085 and TIC13087 can also be compared relative to primary structure (conserved amino acid motifs), by amino acid sequence length and by other characteristics. Characteristics of the TIC13085 and TIC13087 protein toxins are reported in Table 2.

TABLE 2

Selected characteristics of TIC13085 and TIC13087 protein toxins.

| Protein | Molecular Weight (in Daltons) | Amino Acid Length | Isoelectric Point | Charge at PH 7.0 | No. of Hydrophobic Amino Acids | No. of Polar Amino Acids | No. of Strongly Basic (−) Amino Acids | No. of Strongly Acidic Amino Acids |
|---|---|---|---|---|---|---|---|---|
| TIC13085 | 90878.28 | 803 | 4.6994 | −21.5 | 387 | 416 | 88 | 106 |
| TIC13087 | 90495.43 | 802 | 4.3879 | −34.5 | 386 | 416 | 76 | 108 |

Proteins that resemble the TIC13085 or TIC13087 proteins can be identified and compared to each other using various computer-based algorithms known in the art (see Table 1). Amino acid sequence identities reported in this application are a result of a Clustal W alignment using these default parameters: Weight matrix: blossum, Gap opening penalty: 10.0, Gap extension penalty: 0.05, Hydrophilic gaps: On, Hydrophilic residues: GPSNDQERK, Residue-specific gap penalties: On (Thompson, et al (1994) Nucleic Acids Research, 22:4673-4680). Percent amino acid identity is further calculated by the product of 100% multiplied by (amino acid identities/length of subject protein). Other alignment algorithms are also available in the art and provide results similar to those obtained using a Clustal W alignment and are contemplated herein.

It is intended that a protein exhibiting insect inhibitory activity against a Lepidopteran insect species is related to TIC13085 or TIC13087 if the protein is used in a query, e.g., in a Clustal W alignment, and the proteins of the present invention as set forth as SEQ ID NO:2 or SEQ ID NO:4 are identified as hits in such alignment in which the query protein exhibits at least 87% to about 100% amino acid identity along the length of the query protein that is about 88%, 89%, 90%, 91%, 92%, 93%, 94%, 95%, 96%, 97%, 98%, 99%, 100%, or any fraction percentage in this range.

Exemplary TIC13085 and TIC13087 proteins were aligned with each other using a Clustal W algorithm. A pair-wise matrix of percent amino acid sequence identities for each of the protein was created, as reported in Table 1. These toxin proteins exhibited 82% amino acid sequence identity along the entire length of the aligned sequences, and 663 amino acids were positionally identical out of 803 amino acids in TIC13085 versus 802 amino acids in TIC13087.

As described further in the Examples of this application, synthetic nucleic acid sequences encoding TIC13085 and TIC13087 were designed for use in plants, as set forth in SEQ ID NO:5 and SEQ ID NO:6, respectively.

Expression cassettes and vectors containing a recombinant nucleic acid molecule sequence can be constructed and introduced into plants, such as corn, soybean or cotton plant cells in accordance with transformation methods and techniques known in the art. For example, Agrobacterium-mediated transformation is described in U.S. Patent Application Publications 2009/0138985A1 (soybean), 2008/0280361A1 (soybean), 2009/0142837A1 (corn), 2008/0282432 (cotton), 2008/0256667 (cotton), 2003/0110531 (wheat), 2001/0042257 A1 (sugar beet), U.S. Pat. No. 5,750,871 (canola), U.S. Pat. No. 7,026,528 (wheat), and U.S. Pat. No. 6,365,807 (rice), and in Arencibia et al. (1998) Transgenic Res. 7:213-222 (sugarcane). Transformed cells can be regenerated into transformed plants that express TIC13085 and TIC13087 and demonstrate pesticidal activity through bioassays performed in the presence of Lepidopteran pest larvae using plant leaf disks obtained from the transformed plants. Plants can be derived from the plant cells by regeneration, seed, pollen, or meristem transformation techniques. Methods for transforming plants are known in the art.

As an alternative to traditional transformation methods, a DNA sequence, such as a transgene, expression cassette(s), etc., may be inserted or integrated into a specific site or locus within the genome of a plant or plant cell via site-directed integration. Recombinant DNA construct(s) and molecule(s) of this disclosure may thus include a donor template sequence comprising at least one transgene, expression cassette, or other DNA sequence for insertion into the genome of the plant or plant cell. Such donor template for site-directed integration may further include one or two homology arms flanking an insertion sequence (i.e., the sequence, transgene, cassette, etc., to be inserted into the plant genome). The recombinant DNA construct(s) of this disclosure may further comprise an expression cassette(s) encoding a site-specific nuclease and/or any associated protein(s) to carry out site-directed integration. These nuclease expressing cassette(s) may be present in the same molecule or vector as the donor template (in cis) or on a separate molecule or vector (in trans). Several methods for site-directed integration are known in the art involving different proteins (or complexes of proteins and/or guide RNA) that cut the genomic DNA to produce a double strand break (DSB) or nick at a desired genomic site or locus. Briefly as understood in the art, during the process of repairing the DSB or nick introduced by the nuclease enzyme, the donor template DNA may become integrated into the genome at the site of the DSB or nick. The presence of the homology arm(s) in the donor template may promote the adoption and targeting of the insertion sequence into the plant genome during the repair process through homologous recombination, although an insertion event may occur through non-homologous end joining (NHEJ). Examples of site-specific nucleases that may be used include zinc-finger nucleases, engineered or native mega-nucleases, TALEN-endonucleases, and RNA-guided endonucleases (e.g., Cas9 or Cpf1). For methods using RNA-guided site-specific nucleases (e.g., Cas9 or Cpf1), the recombinant DNA construct(s) will also comprise a sequence encoding one or more guide RNAs to direct the nuclease to the desired site within the plant genome.

Recombinant nucleic acid sequence compositions that encode bacterial and plant expressed TIC13085 and TIC13087 proteins can be expressed with recombinant DNA constructs in which a polynucleotide segment with an ORF (open reading frame) encoding the protein is operably linked to genetic regulatory/expression elements such as a promoter and any other regulatory element necessary for controlled expression in the system for which the construct is intended. Non-limiting examples include a plant-functional promoter operably linked to a TIC13085 or TIC13087 protein encoding sequence for expression of the protein in plants or a Bt-functional promoter operably linked to a TIC13085 or TIC13087 protein encoding sequence for expression of the protein in a Bt bacterium or other *Bacillus* species. Other elements can be operably linked to the TIC13085 or TIC13087 protein encoding sequence including, but not limited to, enhancers, operators, introns, untranslated leaders, encoded protein immobilization tags (HIS-tag), translocation peptides (i.e., plastid transit peptides, signal peptides), polypeptide sequences for post-translational modifying enzymes, ribosomal binding sites, transcriptional terminators, and RNAi target sites. Exemplary recombinant polynucleotide molecules provided herewith include, but are not limited to, a heterologous promoter operably linked to a polynucleotide such as SEQ ID NO:1, SEQ ID NO:3, SEQ ID NO:5 and SEQ ID NO:6 that encodes the respective polypeptides or proteins having the amino acid sequence as set forth in SEQ ID NO:2 (encoded by SEQ ID NO:1 and SEQ ID NO:5) and SEQ ID NO:4 (encoded by SEQ ID NO:3 and SEQ ID NO:6). A heterologous promoter can also be operably linked to synthetic DNA coding sequences encoding a plastid targeted TIC13085 or TIC13087. The codons of a recombinant nucleic acid molecule encoding for proteins disclosed herein can be substituted by synonymous codons (known in the art as a silent substitution).

A recombinant DNA construct comprising TIC13085 or TIC13087 protein encoding sequences can further comprise a region of DNA that encodes for one or more insect inhibitory agents which can be configured to concomitantly express or co-express with a DNA sequence encoding a TIC13085 or TIC13087 protein, an insect inhibitory dsRNA molecule, or an ancillary protein. Ancillary proteins include, but are not limited to, co-factors, enzymes, binding-partners, or other agents that function to aid in the effectiveness of an insect inhibitory agent, for example, by aiding its expression, influencing its stability in plants, optimizing free energy for oligomerization, augmenting its toxicity, and increasing its spectrum of activity. An ancillary protein may facilitate the uptake of one or more insect inhibitory agents, for example, or potentiate the toxic effects of the toxic agent.

A recombinant DNA construct can be assembled so that all proteins or dsRNA molecules are expressed from one promoter or each protein or dsRNA molecule is under separate promoter control or some combination thereof. The proteins of this invention can be expressed from a multi-gene expression system in which one or both of TIC13085 or TIC13087 are expressed from a common nucleotide segment which also contains other open reading frames and promoters, depending on the type of expression system selected. For example, a bacterial multi-gene expression system can utilize a single promoter to drive expression of multiply-linked/tandem open reading frames from within a single operon (i.e., polycistronic expression). In another example, a plant multi-gene expression system can utilize multiply-unlinked or linked expression cassettes, each cassette expressing a different protein or other agent such as one or more dsRNA molecules.

Recombinant polynucleotides or recombinant DNA constructs comprising a TIC13085 or TIC13087 protein encoding sequence can be delivered to host cells by vectors, e.g., a plasmid, baculovirus, synthetic chromosome, virion, cosmid, phagemid, phage, or viral vector. Such vectors can be used to achieve stable or transient expression of a TIC13085 or TIC13087 protein encoding sequence in a host cell, or subsequent expression of the encoded polypeptide. An exogenous recombinant polynucleotide or recombinant DNA construct that comprises a TIC13085 or TIC13087 protein encoding sequence and that is introduced into a host cell is referred in this application as a “transgene”.

Transgenic bacteria, transgenic plant cells, transgenic plants, and transgenic plant parts that contain a recombinant polynucleotide that expresses any one or more of TIC13085 or TIC13087 or a related family toxin protein encoding sequence are provided herein. The term “bacterial cell” or “bacterium” can include, but is not limited to, an *Agrobacterium*, a *Bacillus*, an *Escherichia*, a *Salmonella*, a *Pseudomonas, Brevibacillus, Klebsiella, Erwinia*, or a *Rhizobium* cell. The term “plant cell” or “plant” can include but is not limited to a dicotyledonous or monocotyledonous plant. The term “plant cell” or “plant” can also include but is not limited to an alfalfa, banana, barley, bean, broccoli, cabbage, brassica (e.g canola or rapeseed), carrot, cassava, castor, cauliflower, celery, chickpea, Chinese cabbage, citrus, coconut, coffee, corn (including field corn and sweet corn), clover, cotton, a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, Radiata pine, radish, rice, rootstocks, rye, safflower, shrub, sorghum, Southern pine, soybean, spinach, squash, strawberry, sugar beet, sugarcane, sunflower, sweet gum, sweet potato, switchgrass, tea, tobacco, tomato, triticale, turf grass, watermelon, and wheat plant cell or plant. In certain embodiments, transgenic plants and transgenic plant parts regenerated from a transgenic plant cell are provided. In certain embodiments, the transgenic plants can be obtained from a transgenic seed, by cutting, snapping, grinding or otherwise disassociating the part from the plant. In certain embodiments, the plant part can be a seed, a boll, a leaf, a flower, a stem, a root, or any portion thereof, or a non-regenerable portion of a transgenic plant part. As used in this context, a "non-regenerable" portion of a transgenic plant part is a portion that cannot be induced to form a whole plant or that cannot be induced to form a whole plant that is capable of sexual and/or asexual reproduction. In certain embodiments, a non-regenerable portion of a plant part is a portion of a transgenic seed, boll, leaf, flower, stem, or root.

Methods of making transgenic plants that comprise insect, Lepidoptera-inhibitory amounts of a TIC13085 or TIC13087 protein are provided. Such plants can be made by introducing a recombinant polynucleotide that encodes any of the proteins provided in this application into a plant cell, and selecting a plant derived from said plant cell that expresses an insect, Lepidoptera-inhibitory amount of the proteins. Plants can be derived from the plant cells by regeneration, seed, pollen, or meristem transformation techniques. Methods for transforming plants are known in the art.

Processed plant products, wherein the processed product comprises a detectable amount of a TIC13085 or TIC13087, an insect inhibitory segment or fragment thereof, or any distinguishing portion thereof, are also disclosed herein. In certain embodiments, the processed product is selected from the group consisting of plant parts, plant biomass, oil, meal, sugar, animal feed, flour, flakes, bran, lint, hulls, processed seed, and seed. In certain embodiments, the processed product is non-regenerable. The plant product can comprise commodity or other products of commerce derived from a transgenic plant or transgenic plant part, where the commodity or other products can be tracked through commerce by detecting nucleotide segments or expressed RNA or proteins that encode or comprise distinguishing portions of a TIC13085 or TIC13087.

Plants expressing the TIC13085 or TIC13087 proteins can be crossed by breeding with transgenic events expressing other toxin proteins and/or expressing other transgenic traits such as herbicide tolerance genes, genes conferring yield or stress tolerance traits, and the like, or such traits can be combined in a single stacked vector so that the traits are all linked.

As further described in the Examples, TIC13085 or TIC13087 protein-encoding sequences and sequences having a substantial percentage identity to TIC13085 or TIC13087, can be identified using methods known to those of ordinary skill in the art such as polymerase chain reaction (PCR), thermal amplification, and hybridization. For example, the proteins TIC13085 or TIC13087 can be used to produce antibodies that bind specifically to related proteins and can be used to screen for and to find other protein members that are closely related.

Furthermore, nucleotide sequences encoding the TIC13085 or TIC13087 toxin proteins can be used as probes and primers for screening to identify other members of the class using thermal-cycle or isothermal amplification and hybridization methods. For example, oligonucleotides derived from sequences as set forth in SEQ ID NO:5 and SEQ ID NO:6 can be used to determine the presence or absence of a TIC13085 or TIC13087 transgene in a deoxyribonucleic acid sample derived from a commodity product. Given the sensitivity of certain nucleic acid detection methods that employ oligonucleotides, it is anticipated that oligonucleotides derived from sequences as set forth in SEQ ID NO:5 and SEQ ID NO:6 can be used to detect a TIC13085 or TIC13087 transgene in commodity products derived from pooled sources where only a fraction of the commodity product is derived from a transgenic plant containing any of the transgenes. It is further recognized that such oligonucleotides can be used to introduce nucleotide sequence variation in each of SEQ ID NO:1, SEQ ID NO:3, SEQ ID NO:5, and SEQ ID NO:6. Such "mutagenesis" oligonucleotides are useful for identification of TIC13085 and TIC13087 amino acid sequence variants exhibiting a range of insect inhibitory activity or varied expression in transgenic plant host cells.

Nucleotide sequence homologs, e.g., insecticidal proteins encoded by nucleotide sequences that hybridize to each or any of the sequences disclosed in this application under stringent hybridization conditions, are also an embodiment of the present invention. The invention also provides a method for detecting a first nucleotide sequence that hybridizes to a second nucleotide sequence, wherein the first nucleotide sequence (or its reverse complement sequence) encodes a pesticidal protein or pesticidal fragment thereof and hybridizes to the second nucleotide sequence. In such case, the second nucleotide sequence can be any of the nucleotide sequences presented as of SEQ ID NO:1, SEQ ID NO:3, SEQ ID NO:5, or SEQ ID NO:6 under stringent hybridization conditions. Nucleotide coding sequences hybridize to one another under appropriate hybridization conditions, such as stringent hybridization conditions, and the proteins encoded by these nucleotide sequences cross react with antiserum raised against any one of the other proteins. Stringent hybridization conditions, as defined herein, comprise at least hybridization at 42° C. followed by two washes for five minutes each at room temperature with 2×SSC, 0.1% SDS, followed by two washes for thirty minutes each at 65° C. in 0.5×SSC, 0.1% SDS. Washes at even higher temperatures constitute even more stringent conditions, e.g., hybridization conditions of 68° C., followed by washing at 68° C., in 2×SSC containing 0.1% SDS.

One skilled in the art will recognize that, due to the redundancy of the genetic code, many other sequences are capable of encoding such related proteins, and those sequences, to the extent that they function to express pesticidal proteins either in *Bacillus* strains or in plant cells, are embodiments of the present invention, recognizing of course that many such redundant coding sequences will not hybridize under these conditions to the native *Bacillus* sequences encoding TIC13085 and TIC13087 variants. This application contemplates the use of these and other identification methods known to those of ordinary skill in the art, to identify TIC13085 and TIC13087 variant protein-encoding sequences and sequences having a substantial percentage identity to TIC13085 and TIC13087 variants protein-encoding sequences.

This disclosure also contemplates the use of molecular methods known in the art to engineer and clone commercially useful proteins comprising chimeras of proteins from pesticidal proteins; e.g., the chimeras may be assembled from segments of the TIC13085 or TIC13087 proteins to derive additional useful embodiments including assembly of segments of TIC13085 or TIC13087 proteins with segments of diverse proteins different from TIC13085 or TIC13087 proteins and related proteins. The TIC13085 or TIC13087 proteins may be subjected to alignment to each other and to other *Bacillus, Paenibacillus* or other pesticidal proteins (whether or not these are closely or distantly related phylogenetically), and segments of each such protein may be identified that are useful for substitution between the aligned proteins, resulting in the construction of chimeric proteins. Such chimeric proteins can be subjected to pest bioassay analysis and characterized for the presence or absence of increased bioactivity or expanded target pest spectrum compared to the parent proteins from which each such segment in the chimera was derived. The pesticidal activity of the polypeptides may be further engineered for activity to a particular pest or to a broader spectrum of pests by swapping domains or segments with other proteins or by using directed evolution methods known in the art.

Methods of controlling insects, in particular Lepidoptera infestations of crop plants, with the TIC13085 or TIC13087 proteins are disclosed in this application. Such methods can comprise growing a plant comprising an insect- or Lepidoptera-inhibitory amount of a TIC13085 or TIC13087 toxin protein. In certain embodiments, such methods can further comprise any one or more of: (i) applying any composition comprising or encoding a TIC13085 or TIC13087 toxin protein to a plant or a seed that gives rise to a plant; and (ii) transforming a plant or a plant cell that gives rise to a plant with a polynucleotide encoding a TIC13085 or TIC13087 toxin protein. In general, it is contemplated that a TIC13085 or TIC13087 toxin protein can be provided in a composition, provided in a microorganism, or provided in a transgenic plant to confer insect inhibitory activity against Lepidopteran insects.

In certain embodiments, a recombinant nucleic acid molecule of TIC13085 or TIC13087 toxin proteins is the insecticidally active ingredient of an insect inhibitory composition prepared by culturing recombinant *Bacillus* or any other recombinant bacterial cell transformed to express a TIC13085 or TIC13087 toxin protein under conditions suitable to express the TIC13085 or TIC13087 toxin protein. Such a composition can be prepared by desiccation, lyophilization, homogenization, extraction, filtration, centrifugation, sedimentation, or concentration of a culture of such recombinant cells expressing/producing said recombinant polypeptide. Such a process can result in a *Bacillus* or other entomopathogenic bacterial cell extract, cell suspension, cell homogenate, cell lysate, cell supernatant, cell filtrate, or cell pellet. By obtaining the recombinant polypeptides so produced, a composition that includes the recombinant polypeptides can include bacterial cells, bacterial spores, and parasporal inclusion bodies and can be formulated for various uses, including as agricultural insect inhibitory spray products or as insect inhibitory formulations in diet bioassays.

In one embodiment, to reduce the likelihood of resistance development, an insect inhibitory composition comprising TIC13085 or TIC13087 protein can further comprise at least one additional polypeptide that exhibits insect inhibitory activity against the same Lepidopteran insect species, but which is different from the TIC13085 or TIC13087 toxin protein. Possible additional polypeptides for such a composition include an insect inhibitory protein and an insect inhibitory dsRNA molecule. One example for the use of such ribonucleotide sequences to control insect pests is described in Baum, et al. (U.S. Patent Publication 2006/0021087 A1). Such additional polypeptide for the control of Lepidopteran pests may be selected from the group consisting of an insect inhibitory protein, such as, but not limited to, Cry1A (U.S. Pat. No. 5,880,275), Cry1Ab, Cry1Ac, Cry1A.105, Cry1Ae, Cry1B (U.S. Pat. No. 10,525,318), Cry1C (U.S. Pat. No. 6,033,874), Cry1D, Cry1 Da and variants thereof, Cry1E, Cry1F, and Cry1A/F chimeras (U.S. Pat. Nos. 7,070,982; 6,962,705; and 6,713,063), Cry1G, Cry1H, Cry1I, Cry1J, Cry1K, Cry1L, Cry1-type chimeras such as, but not limited to, TIC836, TIC860, TIC867, TIC869, and TIC1100 (International Application Publication WO2016/061391 (A2)), TIC2160 (International Application Publication WO2016/061392(A2)), Cry2A, Cry2Ab (U.S. Pat. No. 7,064,249), Cry2Ae, Cry4B, Cry6, Cry7, Cry8, Cry9, Cry15, Cry43A, Cry43B, Cry51Aa1, ET66, TIC400, TIC800, TIC834, TIC1415, Vip3A, VIP3Ab, VIP3B, AXMI-001, AXMI-002, AXMI-030, AXMI-035, AND AXMI-045 (U.S. Patent Publication 2013-0117884 A1), AXMI-52, AXMI-58, AXMI-88, AXMI-97, AXMI-102, AXMI-112, AXMI-117, AXMI-100 (U.S. Patent Publication 2013-0310543 A1), AXMI-115, AXMI-113, AXMI-005 (U.S. Patent Publication 2013-0104259 A1), AXMI-134 (U.S. Patent Publication 2013-0167264 A1), AXMI-150 (U.S. Patent Publication 2010-0160231 A1), AXMI-184 (U.S. Patent Publication 2010-0004176 A1), AXMI-196, AXMI-204, AXMI-207, AXMI-209 (U.S. Patent Publication 2011-0030096 A1), AXMI-218, AXMI-220 (U.S. Patent Publication 2014-0245491 A1), AXMI-221z, AXMI-222z, AXMI-223z, AXMI-224z, AXMI-225z (U.S. Patent Publication 2014-0196175 A1), AXMI-238 (U.S. Patent Publication 2014-0033363 A1), AXMI-270 (U.S. Patent Publication 2014-0223598 A1), AXMI-345 (U.S. Patent Publication 2014-0373195 A1), AXMI-335 (International Application Publication WO2013/134523(A2)), DIG-3 (U.S. Patent Publication 2013-0219570 A1), DIG-5 (U.S. Patent Publication 2010-0317569 A1), DIG-11 (U.S. Patent Publication 2010-0319093 A1), AfIP-1A and derivatives thereof (U.S. Patent Publication 2014-0033361 A1), AfIP-1B and derivatives thereof (U.S. Patent Publication 2014-0033361 A1), PIP-1APIP-1B (U.S. Patent Publication 2014-0007292 A1), PSEEN3174 (U.S. Patent Publication 2014-0007292 A1), AECFG-592740 (U.S. Patent Publication 2014-0007292 A1), Pput_1063 (U.S. Patent Publication 2014-0007292 A1), DIG-657 (International Application Publication WO2015/195594 A2), Pput_1064 (U.S. Patent Publication 2014-0007292 A1), GS-135 and derivatives thereof (U.S. Patent Publication 2012-0233726 A1), GS153 and derivatives thereof (U.S. Patent Publication 2012-0192310 A1), GS154 and derivatives thereof (U.S. Patent Publication 2012-0192310 A1), GS155 and derivatives thereof (U.S. Patent Publication 2012-0192310 A1), SEQ ID NO:2 and derivatives thereof as described in U.S. Patent Publication 2012-0167259 A1, SEQ ID NO:2 and derivatives thereof as described in U.S. Patent Publication 2012-0047606 A1, SEQ ID NO:2 and derivatives thereof as described in U.S. Patent Publication 2011-0154536 A1, SEQ ID NO:2 and derivatives thereof as described in U.S. Patent Publication 2011-0112013 A1, SEQ ID NO:2 and 4 and derivatives thereof as described in U.S. Patent Publication 2010-0192256 A1, SEQ ID NO:2 and derivatives thereof as described in U.S. Patent Publication 2010-0077507 A1, SEQ ID NO:2 and derivatives thereof as described in U.S. Patent Publication 2010-0077508 A1, SEQ ID NO:2 and derivatives thereof as described in U.S. Patent Publication 2009-0313721 A1, SEQ ID NO:2 or 4 and derivatives thereof as described in U.S. Patent Publication 2010-0269221 A1, SEQ ID NO:2 and derivatives thereof as described in U.S. Pat. No. 7,772,465 (B2), CF161_0085 and derivatives thereof as described in WO2014/008054 A2, Lepidopteran toxic proteins and their derivatives as described in US Patent Publications US2008-0172762 A1, US2011-0055968 A1, and US2012-0117690 A1; SEQ ID NO:2 or 4 and derivatives thereof as described in U.S. Pat. No. 7,510,878(B2), SEQ ID NO:2 or 4 and derivatives thereof as described in U.S. Pat. No. 7,812,129(B1); IPD110Aa and homologs (International Application Publication WO2019/178038 A2); TIC868 (U.S. Pat. No. 10,233,217), Cry1Da1_7 (U.S. Pat. No. 10,059,959), BCW003 (U.S. Pat. No. 10,703,782), TIC1100 (U.S. Pat. No. 10,494,408), TIC867 (U.S. Pat. No. 10,669,317), TIC867_23 (U.S. Pat. No. 10,611,806), TIC6757 (U.S. Pat. No. 10,155,960), TIC7941 (U.S. Patent Publication 2020-0229445 A1), fern toxins toxic to lepidopteran species such as those disclosed in U.S. Pat. No. 10,227,608, and the like.

In other embodiments, such composition/formulation can further comprise at least one additional polypeptide that exhibits insect inhibitory activity to an insect that is not inhibited by an otherwise insect inhibitory protein of the present invention to expand the spectrum of insect inhibition obtained. For example, for the control of Hemipteran pests, combinations of insect inhibitory proteins of the present invention can be used with Hemipteran-active proteins such as TIC1415 (US Patent Publication 2013-0097735 A1), TIC807 (U.S. Pat. No. 8,609,936), TIC834 (U.S. Patent Publication 2013-0269060 A1), AXMI-036 (U.S. Patent Publication 2010-0137216 A1), and AXMI-171 (U.S. Patent Publication 2013-0055469 A1). Further a polypeptide for the control of Coleopteran pests may be selected from the group consisting of an insect inhibitory protein, such as, but not limited to, Cry3Bb (U.S. Pat. No. 6,501,009), Cry1C variants, Cry3A variants, Cry3, Cry3B, Cry34/35, 5307, AXMI134 (U.S. Patent Publication 2013-0167264 A1) AXMI-184 (U.S. Patent Publication 2010-0004176 A1), AXMI-205 (U.S. Patent Publication 2014-0298538 A1), AXMI-207 (U.S. Patent Publication 2013-0303440 A1), AXMI-218, AXMI-220 (U.S. Patent Publication 20140245491A1), AXMI-221z, AXMI-223z (U.S. Patent Publication 2014-0196175 A1), AXMI-279 (U.S. Patent Publication 2014-0223599 A1), AXMI-R1 and variants thereof (U.S. Patent Publication 2010-0197592 A1, TIC407, TIC417, TIC431, TIC807, TIC853, TIC901, TIC1201, TIC3131, DIG-10 (U.S. Patent Publication 2010-0319092 A1), eHIPs (U.S. Patent Application Publication No. 2010/0017914), IP3 and variants thereof (U.S. Patent Publication 2012-0210462 A1), *Pseudomonas* toxin IDP072Aa (US Patent Application Publication No. 2014/055128), and ω-Hexatoxin-Hv1a (U.S. Patent Application Publication US2014-0366227 A1).

Additional polypeptides for the control of Coleopteran, Lepidopteran, and Hemipteran insect pests, which can be combined with the insect inhibitory proteins of the TIC13085 and TIC13087 classes, can be found on the *Bacillus thuringiensis* toxin nomenclature website maintained by Neil Crickmore (on the world wide web at btnomenclature.info). Broadly, it is contemplated that any insect inhibitory protein known to those of ordinary skill in the art can be used in combination with the proteins of the TIC13085 or TIC13087 family both in planta (combined through breeding or molecular stacking) or in a composition or formulation as a biopesticide or combination of biopesticides.

The possibility for insects to develop resistance to certain insecticides has been documented in the art. One insect resistance management strategy is to employ transgenic crops that express two distinct insect inhibitory agents that operate through different modes of action. Therefore, any insects with resistance to either one of the insect inhibitory agents can be controlled by the other insect inhibitory agent. Another insect resistance management strategy employs the use of plants that are not protected to the targeted Lepidopteran pest species to provide a refuge for such unprotected plants. One particular example is described in U.S. Pat. No. 6,551,962, which is incorporated by reference in its entirety.

Other embodiments such as topically applied pesticidal chemistries that are designed for controlling pests that are also controlled by the proteins disclosed herein to be used with proteins in seed treatments, spray on, drip on, or wipe on formulations can be applied directly to the soil (a soil drench), applied to growing plants expressing the proteins disclosed herein, or formulated to be applied to seed containing one or more transgenes encoding one or more of the proteins disclosed. Such formulations for use in seed treatments can be applied with various stickers and tackifiers known in the art. Such formulations can contain pesticides that are synergistic in mode of action with the proteins disclosed, so that the formulation pesticides act through a different mode of action to control the same or similar pests that can be controlled by the proteins disclosed, or that such pesticides act to control pests within a broader host range or plant pest species that are not effectively controlled by the TIC13085 and TIC13087 pesticidal proteins.

The aforementioned composition/formulation can further comprise an agriculturally-acceptable carrier, such as a bait, a powder, dust, pellet, granule, spray, emulsion, a colloidal suspension, an aqueous solution, a *Bacillus* spore/crystal preparation, a seed treatment, a recombinant plant cell/plant tissue/seed/plant transformed to express one or more of the proteins, or bacterium transformed to express one or more of the proteins. Depending on the level of insect inhibitory or insecticidal inhibition inherent in the recombinant polypeptide and the level of formulation to be applied to a plant or diet assay, the composition/formulation can include various by weight amounts of the recombinant polypeptide, e.g. from 0.0001% to 0.001% to 0.01% to 1% to 99% by weight of the recombinant polypeptide.

In view of the foregoing, those of skill in the art should appreciate that changes can be made in the specific aspects which are disclosed and still obtain a like or similar result without departing from the spirit and scope of the invention. Thus, specific structural and functional details disclosed herein are not to be interpreted as limiting. It should be understood that the entire disclosure of each reference cited herein is incorporated within the disclosure of this application.

EXAMPLES

Example 1

Discovery, Cloning, and Expression of TIC13085 and TIC13087

A sequence encoding novel *Bacillus thuringiensis* (Bt) pesticidal proteins were identified, cloned, sequence confirmed, and tested in insect bioassay. The pesticidal protein TIC13085 was identified and isolated from Bt from a plate scrape metagenomics sequencing effort from soil collected from a wheat field in Genessee, Idaho. The pesticidal protein TIC13087 was identified and isolated from Bt from a plate scrape metagenomics sequencing effort from soil collected from a wheat field in Ashley, N. Dak. The environmental samples used for the metagenomic plate scrapes were treated to enrich for endospore forming bacteria and plated at a density of approximately 100 colonies per plate. After culturing, the plates were scraped to provide a DNA sample of each plate. The DNA samples were sequenced and assembled to find potential insecticidal proteins using pFam analysis and homology to known insect toxins. The novel TIC13085 and TIC13087 proteins were identified as belonging to the Vip3 toxin protein class. TIC13085 and TIC13087 are 87.20% and 84.69% identical to Accession WP_119791737, respectively which was derived from *Paenibacillus thiaminolyticus*. The protein of Accession WP_119791737 demonstrated insecticidal activity against Black cutworm (*Agrotis ipsilon*), Corn earworm (*Helicoverpa zea*), Fall armyworm (FAW, *Spodoptera frugiperda*), Beet armyworm (*Spodoptera exigua*), and Tobacco budworm (*Heliothis virescens*) (Estruch et al. (1996) Vip3A, a novel *Bacillus thuringiensis* vegetative insecticidal protein with a wide spectrum of activities against Lepidopteran insects. *Proc. Natl. Acad. Sci.* USA 93:5389-5394).

The TIC13085 and TIC13087 coding sequences were cloned and/or synthesized using methods known in the art and introduced into an *Escherichia coli* (Ec) expression vector in operable linkage with an Ec expressible promoter and a sequence encoding a consecutive series of histidine amino acid residues (i.e., a histidine or "HIS" tag) used for protein purification. Protein preparations of TIC13085 and TIC13087 were used in bioassay.

Example 2

TIC13085 and TIC13087 Demonstrate Lepidopteran Activity in Insect Bioassay

The pesticidal proteins TIC13085 and TIC13087 were expressed in Ec and assayed for toxicity to various species of Lepidoptera. TIC13085 and TIC13087 were also assayed for toxicity to various species of Coleoptera and Hemiptera.

TIC13085 and TIC13087 were assayed for toxicity to the Lepidopteran insect species Black cutworm (BCW, *Agrotis ipsilon*), Corn earworm (CEW, *Helicoverpa zea*, also known as Soybean podworm), Fall armyworm (FAW, *Spodoptera frugiperda*), Southern armyworm (SAW, *Spodoptera eridania*), Soybean looper (SBL, *Chrysodeixis includens*), and Southwestern corn borer (SWC, *Diatraea grandiosella*); the Coleopteran species Western Corn Rootworm (WCR, *Diabrotica virgifera*); and the Hemipteran species Neotropical Brown Stink Bug (NBSB, *Euschistus heros*). Bioassay using recombinant microbial host cell-derived TIC13085 protein demonstrated activity against the Lepidopteran species FAW, SBL, and SWC. Bioassay using microbial host cell-derived TIC13087 protein demonstrated activity against the Lepidopteran species BCW, CEW, and SWC.

Example 3

Synthetic Coding Sequences for TIC13085 and TIC13087 for Use in in Planta Expression Synthetic (artificial) coding sequences were designed for expression in a plant cell encoding TIC13085 and TIC13087.

The synthetic sequences were synthesized, according to methods generally described in U.S. Pat. No. 5,500,365, to avoid certain inimical problem sequences such as ATTTA and A/T rich plant polyadenylation sequences while preserving the amino acid sequence of the native *Bacillus* protein. Plant synthetic coding sequences were designed for TIC13085 (SEQ ID NO:5) and for TIC13087 (SEQ ID NO:6).

Each of the synthetic coding sequences encoding TIC13085 and TIC13087 were introduced into plant transformation vectors using skills known in the art. The resulting transformation vectors used to transform soybean plants comprised a first transgene cassette for expression of the TIC13085 or TIC13087 pesticidal protein which comprised a constitutive promoter, operably linked 5' to a leader, operably linked 5' to a synthetic coding sequence encoding TIC13085 or TIC13087, which was in turn operably linked 5' to a 3' UTR; and a second transgene cassette for the selection of transformed plant cells using spectinomycin selection. The resulting transformation vectors used to transform corn plants comprised a first transgene cassette for expression of the TIC13085 or TIC13087 pesticidal protein which comprised a constitutive promoter, operably linked 5' to a leader, operably linked 5' to an intron, operably linked 5' to a synthetic coding sequence encoding TIC13085 or TIC13087, which was in turn operably linked 5' to a 3' UTR; and a second transgene cassette for the selection of transformed plant cells using glyphosate selection.

Example 4

TIC13085 and TIC13087 Proteins Confer Lepidopteran Toxic Activity when Expressed in Stably Transformed Soybean Plants Binary plant transformation vectors comprising transgene cassettes designed to express TIC13085 and TIC13087 pesticidal protein were cloned using methods known in the art. The resulting vectors were used to stably transform soybean plants. Tissues were harvested from the transformants and used in insect bioassay against various Lepidopteran insect species.

Soybean plants were transformed with the binary transformation vectors as described in Example 3 using an *Agrobacterium*-mediated transformation method. The transformed cells were induced to form plants by methods known in the art. Bioassays using plant leaf disks were performed analogous to those described in U.S. Pat. No. 8,344,207. A single freshly hatched neonate larvae less than one day old was placed on each leaf disc sample and allowed to feed for approximately four days. A non-transformed soybean plant was used to obtain tissue to be used as a negative control. Multiple transformation $R_0$ single-copy insertion events from each binary vector were assessed against Fall armyworm (FAW, *Spodoptera frugiperda*), Southern armyworm (SAW, *Spodoptera eridania*), Soybean looper (SBL, *Chrysodeixis includens*), and Soybean pod worm (SPW, *Helicoverpa zea*). $R_0$ soybean plants transformed with TIC13085 demonstrated activity against FAW, SBL, and SAW. $R_0$ soybean plants transformed with TIC13087 demonstrated activity against SPW.

Selected $R_0$ soybean plants expressing TIC13085 and TIC13087 were allowed to self-pollinate and produce $R_1$ soybean seed. $R_1$ soybean plants expressing TIC13085 were assayed against SAW, SBL, and VBC. $R_1$ soybean plants expressing TIC13085 were assayed against SBL, SPW, and VBC. $R_1$ soybean plants expressing TIC13085 demonstrated activity against SAW, SBL, and VBC. $R_1$ soybean plants expressing TIC13087 demonstrated activity against VBC and SPW.

Example 5

TIC13085 and TIC13087 Expressed in Stably Transformed Corn Plants Confer Lepidopteran Toxic Activity Binary plant transformation vectors comprising transgene cassettes designed to express TIC13085 and TIC13087 pesticidal proteins were cloned using methods known in the art. The resulting vectors were used to stably transform corn plants. Tissues were harvested from the transformants and used in insect bioassay against various Lepidopteran insect species.

Corn plants were transformed with the binary transformation vectors as described in Example 3 using an *Agrobacterium*-mediated transformation method. The transformed cells were induced to form plants by methods known in the art. Bioassays using plant leaf disks were performed analogous to those described in U.S. Pat. No. 8,344,207. A single freshly hatched neonate larvae less than one day old was placed on each leaf disc sample and allowed to feed for approximately four days. A non-transformed corn plant was used to obtain tissue to be used as a negative control. Multiple transformation $R_0$ single-copy insertion events from each binary vector were assessed against Corn earworm (CEW, *Helicoverpa zea*), European corn borer (ECB, *Ostrinia nubilalis*), Fall armyworm (FAW, *Spodoptera frugiperda*), Southwestern corn borer (SWC, *Diatraea grandiosella*), and Black cutworm (BCW, *Agrotis ipsilon*). $R_0$ corn plants expressing TIC13085 from a single copy of the recombinant construct inserted into the plants demonstrated activity against FAW, ECB and SWC. $R_0$ corn plants expressing TIC13087 from a single copy of the recombinant construct inserted into the plants demonstrated activity against CEW, ECB, SWC, and BCW.

Selected $R_0$ corn plants expressing TIC13087 were crossed with a non-transgenic elite corn plant. The resulting $F_1$ heterozygous plants expressing TIC13087 were assayed against Black cutworm (BCW, *Agrotis ipsilon*). $F_1$ heterozygous plants expressing TIC13087 demonstrated activity against BCW.

All of the compositions disclosed and claimed herein can be made and executed without undue experimentation in light of the present disclosure. While the compositions of this invention have been described in terms of the foregoing illustrative embodiments, it will be apparent to those of skill in the art that variations, changes, modifications, and alterations may be applied to the composition described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

All publications and published patent documents cited in the specification are incorporated herein by reference to the same extent as if each individual publication or patent application was specifically and individually indicated to be incorporated by reference.

What is claimed is:

1. A recombinant nucleic acid molecule comprising a heterologous promoter operably linked to a polynucleotide segment encoding a pesticidal protein or pesticidal fragment thereof, wherein:
   a. said pesticidal protein comprises the amino acid sequence of SEQ ID NO:2 or SEQ ID NO:4; or
   b. said pesticidal protein comprises an amino acid sequence having at least 95% amino acid sequence identity to SEQ ID NO:2 or SEQ ID NO:4.

2. The recombinant nucleic acid molecule of claim 1, wherein:
   a. said recombinant nucleic acid molecule is expressed in a plant cell to produce a pesticidally effective amount of the pesticidal protein or pesticidal fragment; or
   b. said recombinant nucleic acid molecule is in operable linkage with a vector, and said vector is selected from the group consisting of a plasmid, phagemid, bacmid, cosmid, and a bacterial or yeast artificial chromosome.

3. The recombinant nucleic acid molecule of claim 1, present within a host cell, wherein said host cell is selected from the group consisting of a bacterial cell and a plant cell.

4. The recombinant nucleic acid molecule of claim 3, wherein said bacterial host cell is from a genus of bacteria selected from the group consisting of: *Agrobacterium, Rhizobium, Bacillus, Brevibacillus, Escherichia, Pseudomonas, Klebsiella, Pantoea,* and *Erwinia.*

5. The recombinant nucleic acid molecule of claim 4, wherein said *Bacillus* is *Bacillus cereus* or *Bacillus thuringiensis,* said *Brevibacillus* is a *Brevibacillus laterosporus,* and said *Escherichia* is a *Escherichia coli*.

6. The recombinant nucleic acid of claim 2, wherein said plant cell is a dicotyledonous or a monocotyledonous plant cell.

7. The recombinant nucleic acid of claim 6, wherein said plant cell is selected from the group consisting of an alfalfa, banana, barley, bean, broccoli, cabbage, brassica, canola, carrot, cassava, castor, cauliflower, celery, chickpea, Chinese cabbage, citrus, coconut, coffee, corn (including field corn and sweet corn), clover, cotton, a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, sweet gum, sweet potato, switchgrass, tea, tobacco, tomato, triticale, turf grass, watermelon, and wheat plant cell.

8. The recombinant nucleic acid molecule of claim 1, wherein said protein exhibits insecticidal activity against a Lepidopteran insect pest.

9. The recombinant nucleic acid molecule of claim 8, wherein said Lepidopteran insect pest is selected from the group consisting of: Black cutworm (*Agrotis ipsilon*), Corn earworm (*Helicoverpa zea*), European corn borer (*Ostrinia nubilalis*), Fall armyworm (*Spodoptera frugiperda*), Southern armyworm (*Spodoptera eridania*), Southwestern corn borer (*Diatraea grandiosella*), and Soybean looper (*Chrysodeixis includens*).

10. A plant comprising the recombinant nucleic acid molecule of claim 1, or a part thereof, wherein a pesticidally effective amount of the pesticidal protein or pesticidal fragment thereof is produced within the cells of said plant.

11. The plant of claim 10, wherein said plant is a monocot plant or a dicot plant, or a part thereof.

12. The plant of claim 10, wherein the plant is selected from the group consisting of an alfalfa, banana, barley, bean, broccoli, cabbage, brassica, canola, carrot, cassava, castor, cauliflower, celery, chickpea, Chinese cabbage, citrus, coconut, coffee, corn, (including field corn and sweet corn), clover, cotton, a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeon pea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, sweet gum, sweet potato, switchgrass, tea, tobacco, tomato, triticale, turf grass, watermelon, and wheat.

13. A seed produced from the plant of claim 10, wherein said seed comprises said recombinant nucleic acid molecule.

14. An insect inhibitory composition comprising the recombinant nucleic acid molecule of claim 1.

15. The insect inhibitory composition of claim 14, further comprising a nucleotide sequence encoding a pesticidal agent that is different from said pesticidal protein or pesticidal fragment thereof.

16. The insect inhibitory composition of claim 15, wherein said pesticidal agent is selected from the group consisting of an insect inhibitory protein, an insect inhibitory dsRNA molecule, a chemical molecule and an ancillary protein, wherein said pesticidal agent is toxic to the same pest as the pesticidal protein or pesticidal fragment thereof.

17. The insect inhibitory composition of claim 15, wherein said pesticidal agent exhibits activity against one or more pest species of the orders Lepidoptera, Coleoptera, or Hemiptera.

18. The insect inhibitory composition of claim 15, wherein said pesticidal agent is selected from the group consisting of a Cry1A, Cry1Ab, Cry1Ac, Cry1A.105, Cry1Ae, Cry1B, Cry1C, Cry1D, Cry1E, Cry1F, Cry1A/F chimeras, Cry1G, Cry1H, Cry1I, Cry1J, Cry1K, Cry1L, Cry2A, Cry2Ab, Cry2Ae, Cry3, Cry3A, Cry3B, Cry4B, Cry6, Cry7, Cry8, Cry9, Cry15, Cry34, Cry35, Cry43A, Cry43B, Cry51Aa1, ET29, ET33, ET34, ET35, ET66, ET70, TIC400, TIC407, TIC417, TIC431, TIC800, TIC807, TIC834, TIC853, TIC900, TIC901, TIC1201, TIC1415, TIC2160, TIC3131, TIC836, TIC860, TIC867, TIC869, TIC1100, VIP3A, VIP3B, VIP3Ab, AXMI-88, AXMI-97, AXMI-102, AXMI-112, AXMI-117, AXMI-100, AXMI-115, AXMI-113, and AXMI-005, AXMI134, AXMI-150, AXMI-171, AXMI-184, AXMI-196, AXMI-204, AXMI-207, AXMI-209, AXMI-205, AXMI-218, AXMI-220, AXMI-221z, AXMI-222z, AXMI-223z, AXMI-224z and AXMI-225z, AXMI-238, AXMI-270, AXMI-279, AXMI-345, AXMI-335, AXMI-R1, IP3, DIG-3, DIG-5, DIG-10, DIG-657, DIG-11 protein, IDP102Aa and homologs thereof, IDP110Aa and homologs thereof, TIC868, Cry1Da1_7, BCW003, TIC1100, TIC867, TIC867_23, TIC6757, TIC7941, IDP072Aa, TIC5290, TIC3668, TIC3669, TIC3670, IDP103 and homologs thereof, PIP-50 and PIP-65 and homologs thereof, PIP-83 and homologs thereof, and Cry1B0.34.

19. The insect inhibitory composition of claim 14, defined as comprising a plant cell that expresses the pesticidal protein from the recombinant nucleic acid molecule of claim 1.

20. A commodity product produced from the plant, or part thereof, of claim 10, wherein the commodity product comprises a detectable amount of said recombinant nucleic acid molecule, said pesticidal protein, or a pesticidal fragment thereof.

21. The commodity product of claim 20, selected from the group consisting of commodity corn bagged by a grain handler, corn flakes, corn cakes, corn flour, corn meal, corn syrup, corn oil, corn silage, corn starch, corn cereal, and corresponding soybean, rice, wheat, sorghum, pigeon pea, peanut, fruit, melon, and vegetable commodity products including, juices, concentrates, jams, jellies, marmalades, whole or processed cotton seed, lint, seeds and plant parts processed for feed or food, fiber, paper, biomasses, whole or processed soybean seed, soybean protein, soybean meal, soybean flour, soybean flakes, soybean bran, soybean milk, soybean cheese, soybean wine, animal feed comprising soybean, paper comprising soybean, cream comprising soybean, soybean biomass, and fuel products produced using soybean plants and soybean plant parts.

22. A method of producing a progeny seed comprising the recombinant nucleic acid molecule of claim 1, the method comprising:
   a. planting a first seed comprising the recombinant nucleic acid molecule;
   b. growing a plant from the seed of step a; and
   c. harvesting the progeny seed from the plant, wherein said harvested seed comprises said recombinant nucleic acid molecule.

23. A plant resistant to insect infestation, wherein the cells of said plant comprise the recombinant nucleic acid molecule of claim 1.

24. A method for controlling a Lepidopteran species pest infestation, said method comprising contacting the pest with the insect inhibitory composition of claim 14.

25. A method of detecting the presence of the recombinant nucleic acid molecule of claim 1 in a sample comprising plant genomic DNA, comprising:
   a. contacting said sample with a nucleic acid probe that hybridizes under stringent hybridization conditions with genomic DNA from a plant comprising the recombinant nucleic acid molecule of claim 1, and does not hybridize under such hybridization conditions with genomic DNA from an otherwise isogenic plant that does not comprise the recombinant nucleic acid molecule of claim 1, wherein said probe is homologous or complementary to SEQ ID NO:5 or SEQ ID NO:6; or a sequence that encodes a pesticidal protein comprising an amino acid sequence having at least amino acid sequence identity to SEQ ID NO:2 or SEQ ID NO:4;
   b. hybridizing said probe with said polynucleotide segment; and
   c. detecting hybridization of said probe with said with said polynucleotide segment.

26. The recombinant nucleic acid molecule of claim 1, wherein said pesticidal protein comprises the amino acid sequence of SEQ ID NO:2.

27. The recombinant nucleic acid molecule of claim 1, wherein said pesticidal protein comprises the amino acid sequence of SEQ ID NO:4.

28. The recombinant nucleic acid molecule of claim 1, wherein said pesticidal protein comprises an amino acid sequence having at least 95% amino acid sequence identity to SEQ ID NO:2.

29. The recombinant nucleic acid molecule of claim 1, wherein said pesticidal protein comprises an amino acid sequence having at least 95% amino acid sequence identity to or SEQ ID NO:4.

* * * * *